(12) United States Patent
Glenn et al.

(10) Patent No.: US 7,818,083 B2
(45) Date of Patent: Oct. 19, 2010

(54) AUTOMATED WASHING SYSTEM WITH COMPLIANCE VERIFICATION AND AUTOMATED COMPLIANCE MONITORING REPORTING

(75) Inventors: James Glenn, Denver, CO (US); Douglas Swartz, Lakewood, CO (US)

(73) Assignee: Resurgent Health & Medical, LLC, Golden, CO (US)

(*) Notice: Subject to any disclaimer, the term of this patent is extended or adjusted under 35 U.S.C. 154(b) by 107 days.

(21) Appl. No.: 11/852,099

(22) Filed: Sep. 7, 2007

(65) Prior Publication Data

US 2008/0103636 A1    May 1, 2008

Related U.S. Application Data

(60) Provisional application No. 60/863,753, filed on Oct. 31, 2006, provisional application No. 60/909,280, filed on Mar. 30, 2007.

(51) Int. Cl.
*G06F 19/00* (2006.01)
(52) U.S. Cl. .......................... 700/108; 705/2
(58) Field of Classification Search .............. 700/9, 700/108, 109, 111; 705/1, 7, 14, 500, 2; 134/56 R, 61
See application file for complete search history.

(56) References Cited

U.S. PATENT DOCUMENTS

| | | | |
|---|---|---|---|
| 2,325,008 A | 7/1943 | Gruett |
| 2,386,455 A | 10/1945 | Green |
| 2,522,928 A | 9/1950 | Carroll |
| 2,647,801 A | 8/1953 | Lycan |
| 2,769,547 A | 11/1956 | Hirsch |
| 2,789,865 A | 4/1957 | Shannon |
| 2,826,763 A | 3/1958 | Bass |
| 2,896,856 A | 7/1959 | Kravits |
| 3,059,815 A | 10/1962 | Parsons, Jr. |
| 3,081,471 A | 3/1963 | Newell |
| 3,220,424 A | 11/1965 | Nelson |

(Continued)

FOREIGN PATENT DOCUMENTS

DE        19903079        8/2000

(Continued)

OTHER PUBLICATIONS

International Search Report for International (PCT) Patent Application No. PCT/US2007/83221, mailed Aug. 6, 2008.

(Continued)

*Primary Examiner*—Albert DeCady
*Assistant Examiner*—Chad Rapp
(74) *Attorney, Agent, or Firm*—Sheridan Ross P.C.

(57) ABSTRACT

A system is provided for providing automated washing and verifying compliance of use. The system provides for identifying individual users of one or more cleaning stations through various technologies, such as RFID. Individual's use of cleaning stations is monitored to determine compliance with hand-washing requirements. A compliance report may be generated based on data associated with one or more individuals' use of the cleaning station(s). Educational and/or entertainment content may be displayed to the user when he or she is using the cleaning station. Additionally, the cleaning station may identify containers having authorized consumables such as soap or disinfectant. Optional automated collection and forwarding of hygiene compliance information is performed to provide compliance monitors, such as a regulatory agency, with such information.

25 Claims, 13 Drawing Sheets

Data Management Module Report
1000

| Enterprise ID # | Station ID # | User ID # | Date | Time | Facility | Wash Cycle Complete | Compliance Monitor ID # |
|---|---|---|---|---|---|---|---|
| 123456 | 111 | 11111 | 7/5/2007 | 8:00 AM | A | Y | Fed #1 |
| 123456 | 112 | 22222 | 7/8/2007 | 9:15 AM | C | Y | Fed #2 |
| 123456 | 113 | 33333 | 7/13/2007 | 8:45 AM | B | Y | State #1 |
| 123456 | 114 | 44444 | 7/16/2007 | 7:30 AM | C | N | Local #1 |
| 123456 | 115 | 55555 | 7/16/2007 | 1:20 PM | D | Y | Local #2 |

U.S. PATENT DOCUMENTS

| | | |
|---|---|---|
| 3,243,264 A | 3/1966 | Hickey |
| 3,437,274 A | 4/1969 | Apri |
| 3,529,774 A | 9/1970 | Apri |
| 3,639,844 A | 2/1972 | Karklys |
| 3,647,147 A | 3/1972 | Cook |
| 3,699,984 A | 10/1972 | Davis |
| 3,744,149 A | 7/1973 | Helbling |
| 3,754,559 A | 8/1973 | Seiwert |
| 3,757,806 A | 9/1973 | Baaskar et al. |
| 3,817,651 A | 6/1974 | Law et al. |
| 3,844,278 A | 10/1974 | Weider |
| 3,881,328 A | 5/1975 | Kleimola et al. |
| 3,918,117 A | 11/1975 | Plante |
| 3,918,987 A | 11/1975 | Kopfer |
| 3,967,478 A | 7/1976 | Guinn |
| 3,992,730 A | 11/1976 | Davis |
| 3,997,873 A | 12/1976 | Thornton |
| 4,001,599 A | 1/1977 | Karklys |
| 4,020,856 A | 5/1977 | Masterson |
| 4,073,301 A | 2/1978 | Mackinnon |
| 4,120,180 A | 10/1978 | Jedora |
| 4,137,929 A | 2/1979 | Grossman |
| 4,219,367 A | 8/1980 | Cary, Jr. et al. |
| 4,275,385 A | 6/1981 | White |
| 4,295,233 A | 10/1981 | Hinkel et al. |
| 4,398,310 A | 8/1983 | Lienhard |
| 4,402,331 A | 9/1983 | Taldo et al. |
| 4,453,286 A | 6/1984 | Wieland |
| 4,496,519 A | 1/1985 | McGuire |
| 4,509,543 A | 4/1985 | Livingston et al. |
| 4,601,064 A | 7/1986 | Shipley |
| 4,606,085 A | 8/1986 | Davies |
| 4,606,500 A | 8/1986 | Mussler et al. |
| 4,670,010 A | 6/1987 | Dragone |
| 4,688,585 A | 8/1987 | Vetter |
| 4,769,863 A | 9/1988 | Tegg et al. |
| 4,817,651 A | 4/1989 | Crisp et al. |
| 4,896,144 A | 1/1990 | Bogstad |
| 4,916,435 A | 4/1990 | Fuller |
| 4,921,211 A | 5/1990 | Novak et al. |
| 4,925,495 A | 5/1990 | Crisp et al. |
| 4,942,631 A | 7/1990 | Rosa |
| 4,999,613 A | 3/1991 | Williamson et al. |
| 5,016,172 A | 5/1991 | Dessertine |
| 5,031,258 A | 7/1991 | Shaw |
| 5,060,323 A | 10/1991 | Shaw |
| 5,074,322 A | 12/1991 | Jaw |
| RE33,810 E | 2/1992 | Strieter |
| 5,086,526 A | 2/1992 | Van Marcke |
| 5,119,104 A | 6/1992 | Heller |
| 5,184,642 A | 2/1993 | Powell |
| 5,193,563 A | 3/1993 | Melech |
| 5,199,118 A | 4/1993 | Cole et al. |
| 5,202,666 A | 4/1993 | Knippscheer |
| 5,238,749 A | 8/1993 | Cueman et al. |
| 5,257,423 A | 11/1993 | Jacobsen et al. |
| 5,265,628 A | 11/1993 | Sage et al. |
| 5,291,399 A | 3/1994 | Chaco |
| 5,340,581 A | 8/1994 | Tseng et al. |
| 5,387,993 A | 2/1995 | Heller et al. |
| RE35,035 E | 9/1995 | Shipley |
| 5,455,851 A | 10/1995 | Chaco et al. |
| 5,465,082 A | 11/1995 | Chaco |
| 5,503,840 A | 4/1996 | Jacobson et al. |
| 5,515,426 A | 5/1996 | Yacenda et al. |
| 5,548,637 A | 8/1996 | Heller et al. |
| 5,561,412 A | 10/1996 | Novak et al. |
| 5,572,195 A | 11/1996 | Heller et al. |
| 5,594,786 A | 1/1997 | Chaco et al. |
| 5,601,100 A | 2/1997 | Kawakami et al. |
| 5,610,589 A | 3/1997 | Evans et al. |
| 5,633,742 A | 5/1997 | Shipley |
| 5,670,945 A | 9/1997 | Applonie |
| 5,689,229 A | 11/1997 | Chaco et al. |
| 5,695,091 A | 12/1997 | Winings et al. |
| 5,699,038 A | 12/1997 | Ulrich et al. |
| 5,702,115 A | 12/1997 | Pool |
| 5,727,579 A | 3/1998 | Chardack |
| 5,745,272 A | 4/1998 | Shipley |
| 5,765,242 A | 6/1998 | Marciano |
| 5,774,865 A | 6/1998 | Glynn |
| 5,781,942 A | 7/1998 | Allen et al. |
| 5,793,653 A * | 8/1998 | Segal .................. 702/176 |
| 5,808,553 A | 9/1998 | Cunningham |
| 5,812,059 A | 9/1998 | Shaw et al. |
| 5,818,617 A | 10/1998 | Shipley |
| 5,822,418 A | 10/1998 | Yacenda et al. |
| 5,822,544 A | 10/1998 | Chaco et al. |
| 5,823,447 A | 10/1998 | Maybach |
| 5,838,223 A | 11/1998 | Gallant et al. |
| 5,845,225 A | 12/1998 | Mosher |
| 5,860,437 A | 1/1999 | Fernie |
| 5,863,497 A | 1/1999 | Dirksing |
| 5,870,015 A | 2/1999 | Hinkel |
| 5,900,067 A | 5/1999 | Jones |
| 5,900,801 A | 5/1999 | Heagle et al. |
| 5,924,148 A | 7/1999 | Flowers, Sr. |
| 5,939,974 A | 8/1999 | Heagle et al. |
| 5,945,068 A | 8/1999 | Ferone |
| 5,945,910 A * | 8/1999 | Gorra .................. 340/573.1 |
| 5,952,924 A | 9/1999 | Evans et al. |
| 5,954,069 A | 9/1999 | Foster |
| 5,966,573 A | 10/1999 | Yu et al. |
| 5,966,753 A | 10/1999 | Gauthier et al. |
| 5,972,126 A | 10/1999 | Fernie |
| 5,979,500 A | 11/1999 | Jahrling et al. |
| 5,992,430 A | 11/1999 | Chardack et al. |
| 6,029,600 A | 2/2000 | Davis |
| 6,031,461 A | 2/2000 | Lynn |
| 6,037,871 A | 3/2000 | Babylon |
| 6,038,331 A | 3/2000 | Johnson |
| 6,038,519 A | 3/2000 | Gauthier et al. |
| 6,110,292 A | 8/2000 | Jewett et al. |
| 6,125,482 A | 10/2000 | Foster |
| 6,131,587 A | 10/2000 | Chardack et al. |
| 6,147,607 A | 11/2000 | Lynn |
| 6,161,227 A | 12/2000 | Bargenquast |
| 6,176,941 B1 | 1/2001 | Jewett et al. |
| 6,195,588 B1 | 2/2001 | Gauthier et al. |
| 6,211,788 B1 | 4/2001 | Lynn et al. |
| 6,232,870 B1 | 5/2001 | Garber et al. |
| 6,235,351 B1 | 5/2001 | DiMarzio et al. |
| 6,236,317 B1 * | 5/2001 | Cohen et al. ............ 340/573.1 |
| 6,236,953 B1 | 5/2001 | Segal |
| 6,268,797 B1 | 7/2001 | Berube et al. |
| 6,278,372 B1 | 8/2001 | Velasco, Jr. et al. |
| 6,317,717 B1 | 11/2001 | Lindsey et al. |
| 6,335,686 B1 | 1/2002 | Goff et al. |
| 6,344,794 B1 | 2/2002 | Ulrich et al. |
| 6,351,866 B1 | 3/2002 | Bragulla |
| 6,392,546 B1 * | 5/2002 | Smith .................. 340/573.1 |
| 6,399,853 B1 | 6/2002 | Roe et al. |
| 6,404,837 B1 | 6/2002 | Thompson et al. |
| 6,413,921 B1 | 7/2002 | Childers et al. |
| 6,417,773 B1 | 7/2002 | Vlahos et al. |
| 6,424,262 B2 | 7/2002 | Garber et al. |
| 6,426,701 B1 | 7/2002 | Levy et al. |
| 6,431,189 B1 | 8/2002 | Deibert |
| 6,448,886 B2 | 9/2002 | Garber et al. |
| 6,462,656 B2 | 10/2002 | Ulrich et al. |
| 6,486,780 B1 | 11/2002 | Garber et al. |
| 6,523,193 B2 | 2/2003 | Saraya |
| 6,524,390 B1 | 2/2003 | Jones |
| 6,539,393 B1 | 3/2003 | Kabala |

| | | |
|---|---|---|
| 6,542,568 B1 | 4/2003 | Howes, Jr. et al. |
| 6,577,240 B2 | 6/2003 | Armstrong |
| 6,600,420 B2 | 7/2003 | Goff et al. |
| 6,663,719 B2 | 12/2003 | Shinozaki et al. |
| 6,671,890 B2 | 1/2004 | Nishioka |
| 6,706,243 B1 | 3/2004 | Sias et al. |
| 6,707,873 B2 | 3/2004 | Thompson et al. |
| 6,727,818 B1 | 4/2004 | Wildman et al. |
| 6,733,595 B1 | 5/2004 | Grillo |
| 6,759,959 B2 | 7/2004 | Wildman |
| 6,768,419 B2 | 7/2004 | Garber et al. |
| 6,825,763 B2 | 11/2004 | Ulrich et al. |
| 6,832,916 B2 | 12/2004 | Collopy |
| 6,882,278 B2 * | 4/2005 | Winings et al. .......... 340/573.1 |
| 6,883,563 B2 | 4/2005 | Smith |
| 6,892,143 B2 | 5/2005 | Howes, Jr. et al. |
| 6,902,397 B2 | 6/2005 | Farrell et al. |
| 6,938,282 B2 | 9/2005 | Yamamoto |
| 6,956,498 B1 | 10/2005 | Gauthier et al. |
| 6,970,574 B1 | 11/2005 | Johnson |
| D512,648 S | 12/2005 | Smith et al. |
| 6,975,231 B2 * | 12/2005 | Lane et al. ............... 340/573.1 |
| 6,992,561 B2 | 1/2006 | Sandt et al. |
| 7,010,369 B2 | 3/2006 | Borders et al. |
| 7,015,816 B2 | 3/2006 | Wildman et al. |
| 7,020,508 B2 | 3/2006 | Stivoric et al. |
| 7,023,980 B2 | 4/2006 | Lenard et al. |
| 7,080,061 B2 | 7/2006 | Kabala |
| 7,107,631 B2 | 9/2006 | Lang et al. |
| 7,113,094 B2 | 9/2006 | Garber et al. |
| 7,119,688 B2 | 10/2006 | Wildman |
| 7,120,800 B2 | 10/2006 | Ginter et al. |
| 7,123,151 B2 | 10/2006 | Garber et al. |
| 7,150,293 B2 | 12/2006 | Jonte |
| 7,174,577 B2 | 2/2007 | Jost et al. |
| 7,242,306 B2 | 7/2007 | Wildman et al. |
| 7,242,307 B1 * | 7/2007 | LeBlond et al. .......... 340/573.1 |
| 7,248,933 B2 | 7/2007 | Wildman |
| 7,270,268 B2 | 9/2007 | Garber et al. |
| 7,271,719 B2 | 9/2007 | Ku et al. |
| 7,271,728 B2 * | 9/2007 | Taylor et al. ............. 340/573.1 |
| 7,293,645 B2 * | 11/2007 | Harper et al. ................ 206/205 |
| 7,423,533 B1 * | 9/2008 | LeBlond et al. .......... 340/572.1 |
| 7,443,305 B2 | 10/2008 | Verdiramo |
| 2002/0019709 A1 | 2/2002 | Segal |
| 2002/0104083 A1 | 8/2002 | Hendricks et al. |
| 2002/0135486 A1 | 9/2002 | Brohagen et al. |
| 2002/0175182 A1 | 11/2002 | Matthews |
| 2003/0069815 A1 | 4/2003 | Eisenberg et al. |
| 2003/0089771 A1 | 5/2003 | Cybulski et al. |
| 2003/0197122 A1 | 10/2003 | Faiola et al. |
| 2004/0083547 A1 | 5/2004 | Mercier |
| 2004/0133081 A1 | 7/2004 | Teller et al. |
| 2004/0150527 A1 | 8/2004 | Harper et al. |
| 2004/0255409 A1 | 12/2004 | Hilscher et al. |
| 2005/0134465 A1 | 6/2005 | Rice et al. |
| 2005/0136949 A1 | 6/2005 | Barnes |
| 2005/0139239 A1 | 6/2005 | Prae |
| 2005/0147526 A1 | 7/2005 | Hishida |
| 2005/0151641 A1 | 7/2005 | Ulrich et al. |
| 2005/0171634 A1 * | 8/2005 | York et al. .................. 700/231 |
| 2005/0248461 A1 | 11/2005 | Lane et al. |
| 2006/0019200 A1 | 1/2006 | Vermeersch et al. |
| 2006/0122474 A1 | 6/2006 | Teller et al. |
| 2006/0132316 A1 | 6/2006 | Wildman et al. |
| 2006/0224051 A1 | 10/2006 | Teller et al. |
| 2006/0229891 A1 | 10/2006 | Grier |
| 2006/0231568 A1 | 10/2006 | Lynn et al. |
| 2006/0241396 A1 | 10/2006 | Fabian et al. |
| 2006/0264730 A1 | 11/2006 | Stivoric et al. |
| 2007/0011893 A1 | 1/2007 | Garber et al. |
| 2007/0020212 A1 | 1/2007 | Bernal et al. |
| 2007/0247316 A1 | 10/2007 | Wildman et al. |
| 2007/0257803 A1 | 11/2007 | Munro et al. |
| 2007/0273525 A1 | 11/2007 | Garber et al. |
| 2008/0001763 A1 | 1/2008 | Raja et al. |
| 2008/0031838 A1 | 2/2008 | Bolling |
| 2009/0083970 A1 | 4/2009 | Barnhill et al. |
| 2009/0084407 A1 | 4/2009 | Glenn et al. |
| 2009/0084414 A1 | 4/2009 | Barnhill et al. |
| 2009/0084417 A1 | 4/2009 | Barnhill et al. |
| 2009/0090389 A1 | 4/2009 | Barnhill et al. |
| 2009/0090390 A1 | 4/2009 | Barnhill et al. |
| 2009/0094814 A1 | 4/2009 | Barnhill et al. |
| 2009/0107528 A1 | 4/2009 | Barnhill et al. |
| 2010/0095983 A1 | 4/2010 | Barnhill et al. |
| 2010/0097224 A1 | 4/2010 | Prodanovich et al. |
| 2010/0155420 A1 | 6/2010 | Glenn et al. |

FOREIGN PATENT DOCUMENTS

| | | |
|---|---|---|
| EP | 0396039 | 11/1990 |
| EP | 0616658 | 9/1994 |
| EP | 0758702 | 2/1997 |
| EP | 1872802 | 1/2008 |
| EP | 1935515 | 6/2008 |
| FR | 2659217 | 9/1991 |
| GB | 2324397 | 10/1998 |
| JP | 5-329065 | 12/1993 |
| WO | WO 80/01983 | 10/1980 |
| WO | WO 93/10311 | 5/1993 |
| WO | WO 03/086274 | 10/2003 |

OTHER PUBLICATIONS

Written Opinion for International (PCT) Patent Application No. PCT/US2007/83221, mailed Aug. 6, 2008.
U.S. Appl. No. 11/617,024, filed Dec. 28, 2006, Prodanovich.
U.S. Appl. No. 11/617,177, filed Dec. 28, 2006, Glenn.
U.S. Appl. No. 11/689,582, filed Mar. 22, 2007, Barnhill.
U.S. Appl. No. 11/829,764, filed Jul. 27, 2007, Barnhill.
U.S. Appl. No. 11/829,769, filed Jul. 27, 2007, Barnhill.
U.S. Appl. No. 11/829,775, filed Jul. 27, 2007, Barnhill.
U.S. Appl. No. 11/829,781, filed Jul. 27, 2007, Barnhill.
U.S. Appl. No. 11/829,783, filed Jul. 27, 2007, Barnhill.
"HandGiene" available at http://handgienecorp.com/index.jsp, printed Nov. 2, 2009, pp. 1-2.
Notice of Allowance for U.S. Appl. No. 11/617,177, mailed Oct. 30, 2009.
U.S. Appl. No. 12/432,693, filed Apr. 29, 2004, Barnhill.
U.S. Appl. No. 12/432,698, filed Apr. 29, 2009, Barnhill et al.
U.S. Appl. No. 12/432,711, filed Apr. 29, 2009, Glenn, et al.
U.S. Appl. No. 12/432,716, filed Apr. 29, 2009, Barnhill
U.S. Appl. No. 12/432,718, filed Apr. 29, 2009, Barnhill, et al.
"Case Study: FL hospital used IT to monitor hand washing", FierceHealthIT website, dated Aug. 3, 2009, available at http://www.fiercehealthit.com/node/8503/print, printed on Aug. 11, 2009, p. 1.
"Michigan IT Companies Helping the University of Miami Center for Patient Safety Tackle a Leading Cause of Death Using an RTLS Solution to Monitor Staff Hand-Washing Compliance", prnewswire website, dated Jul. 29, 2009, available at http://news.prnewswire.com/DisplayReleaseContent.aspx?ACCT=104&STORY=/www/story/07-29-2009/0005068398&EDATE, printed on Aug. 10, 2009, pp. 1-2.
Search Results, Mar. 2007, 27 pages.
"Hygreen The Intelligent Hand Hygiene Solution", Xhale, Inc., date unknown, 2 pages.
"HyGreen: How it Works",available at http://www.xhale.com/hygreen/solution/How.asp,printed Jul. 14, 2009, pp. 1-2.

"HyGreen: Sample Reporting", available at http://www.xhale.com/hygreen/solution/Reporting.asp, printed Jul. 14, 2009, pp. 1-3.

Background section of the above-captioned application (previously provided).

International Preliminary Report on Patentability for International (PCT) Patent Application No. PCT/US2007/83221, mailed May 14, 2009.

Official Action for U.S. Appl. No. 11/617,177, mailed Feb. 19, 2009.

European Search Report for European Patent Application No. 07863731.1, mailed May 11, 2010.

Official Action for European Patent Application No. 07863731.1, mailed May 31, 2010.

\* cited by examiner

Cleaning Station-Use Record 400

| Employee Name | Time Stamp | Duration | Date | Compliance |
|---|---|---|---|---|
| Janet Smith | 08:00:00 a.m. | 10 secs | 5/21/2006 | Y |
| Bill Powers | 09:00:23 a.m. | 5 secs | 5/21/2006 | N |
| Jason Williams | 10:07:40 a.m. | 12 secs | 5/21/2006 | Y |
| Judy Jones | 11:10:05 a.m. | 11 secs | 5/21/2006 | Y |
| Sandra Collins | 11:20:31 a.m. | 6 secs | 5/21/2006 | N |

*Fig. 4*

Employee Record 340

| Employee Name | Hand Washing Statistics | Current Training Segment | Preferred Entertainment Content | Allergy |
|---|---|---|---|---|
| Sandra Collins | 94% | 3 | Sport | None |
| Bill Forbes | 97% | 5 | News | Solution A |
| Jane Givens | 91% | 4 | Sports | None |
| Judy Jones | 99% | 9 | News | None |
| Bill Powers | 85% | 1 | News | None |
| Jane Smith | 95% | 8 | Sports | None |
| Jason Williams | 90% | 4 | News | None |

*Fig. 5A*

Lookup Table 520

| Employee Identifier | Employee Type | Protocol Identifier |
|---|---|---|
| 11111 | 1 | 1 |
| 22222 | 1 | 1 |
| 33333 | 2 | 2 |
| 44444 | 3 | 3 |
| 55555 | 1 | 1 |
| 66666 | 4 | 0 |
| ⋮ | ⋮ | ⋮ |

Compliance Report 640

| Employee Name | Time | Date | Location | Full Cycle |
|---|---|---|---|---|
| Janet Smith | 8:00 a.m. | 5/21/2006 | A | Y |
| Bill Powers | 9:00 a.m. | 5/21/2006 | A | N |
| Bill Forbes | 10:00 a.m. | 5/21/2006 | C | N |
| Jason Williams | 10:07 a.m. | 5/21/2006 | A | Y |
| Jane Givens | 10:30 a.m. | 5/21/2006 | D | N |
| Judy Jones | 11:10 a.m. | 5/21/2006 | A | Y |
| Sandra Collins | 11:20 a.m. | 5/21/2006 | A | Y |

*Fig. 7*

Data Management Module Report
1000

| Enterprise ID # | Station ID # | User ID # | Date | Time | Facility | Wash Cycle Complete | Compliance Monitor ID # |
|---|---|---|---|---|---|---|---|
| 123456 | 111 | 11111 | 7/5/2007 | 8:00 AM | A | Y | Fed #1 |
| 123456 | 112 | 22222 | 7/8/2007 | 9:15 AM | C | Y | Fed #2 |
| 123456 | 113 | 33333 | 7/13/2007 | 8:45 AM | B | Y | State #1 |
| 123456 | 114 | 44444 | 7/16/2007 | 7:30 AM | C | N | Local #1 |
| 123456 | 115 | 55555 | 7/16/2007 | 1:20 PM | D | Y | Local #2 |

*Fig. 10*

| Geographic Location Information *1200* | Compliance Monitor Designation *1202* | Compliance Data Required *1204* | Required Reporting Frequency *1208* | Report Requirements *1212* |
|---|---|---|---|---|
| 1111 | A | Number Washes/Unit, Percent Compliant | Monthly | GGGG |
| 1111 | B | Number Washes/Employee, Percent Compliant | Weekly | HHHH |
| | | ... | ... | |

*Fig. 12*

AUTOMATED WASHING SYSTEM WITH COMPLIANCE VERIFICATION AND AUTOMATED COMPLIANCE MONITORING REPORTING

CROSS REFERENCE TO RELATED APPLICATIONS

This application claims the benefit of U.S. Provisional Application No. 60/863,753, filed Oct. 31, 2006 and the benefit of U.S. Provisional Application No. 60/909,280, filed Mar. 30, 2007 the entire contents of both applications are incorporated herein by reference in their entirety.

FIELD

The present invention relates to automated washing systems, and more particularly, to automated washing systems comprising a way of monitoring and/or verifying user participation. Methods of providing compliance verification are also provided.

BACKGROUND

The importance of cleanliness has long been recognized, particularly in the fields of heath-care, food preparation, and laboratories, to name but a few. The practice of surgical scrubbing by surgeons and other operating room personnel is probably the epitome of efforts to cleanse the hands and forearms of persons working in sterile environments. Although manual hand-washing can appear effective, medical experts have concluded that automated hand-washing increases hand-washing compliance and reduces the risk of infection.

Touchless automated hand-washing devices are designed to wash the hands of the user and provide the proper amount of antimicrobial solution in a set time. Additionally, these systems diminish the deterrent effects of friction and irritation associated with frequent manual hand-washing. Notwithstanding the benefits and convenience of automated washing devices, difficulties still exist with verifying employee or staff use of the washing apparatus. Accordingly, it would be advantageous to have a system that provides automated washing with a way of verifying usage by the intended users.

In addition to the foregoing, problems also exist with verifying that the proper soap solutions or disinfectants are being used in a cleaning station. In addition, problems exist with assessing whether a user has an allergy where the user should not use a certain type of soap or disinfectant provided in a cleaning station. In addition, problems exist in providing a solution in a cleaning station to avoid an allergy of a user. Also, problems exist in providing user specific formulations that address, for example, the user's specific job duties. In addition, problems exist in motivating users to stay at a cleaning station for its entire cleaning cycle. Also, problems exist in providing information to a manager or administrator regarding monitoring one or more cleaning stations, wherein the monitoring may include review of data directed to addressing one or more of the above noted problems.

U.S. Pat. Nos. 7,015,816, 6,727,818 and United Stated Patent Application Publication No. 2006/0132316 are directed to systems that in part address the problems outlined above. The summary of each document indicates that the disclosed systems are directed to monitoring or gathering information on locations of person, equipment, and/or activities associated with a facility. The gathered information is used to evaluate compliance with hygiene requirements as defined by a hygiene policy for a facility. These systems suffer from several drawbacks including facility (e.g. hospital) liability concerns introduced by the disclosed monitoring methods. These systems also make no allowance for people with no hand-washing requirements such as visitors to the facility. Additionally, these systems include a burdensome system of in/out zones, do not provide for automatic reporting, and do not include hand-washing requirements that are specific to a person's job title. Furthermore, these systems do not disclose a system for automatically providing hygiene compliance information to a regulatory body. These shortcomings are addressed by the various embodiments of the present invention.

SUMMARY

In accordance with embodiments of the present invention, a Radio Frequency Identification ("RFID") system is disclosed for use in connection with an automated hand-washing station. However, as described herein, other identifying technologies are appropriate, and such technologies are encompassed by the scope of the present invention. Examples include bar codes, biometric technology and the like. It is to be understood therefore, that RFID is used as an example and is not intended to limit the scope of the present invention.

The system is operable to record and report on user compliance with hand-washing requirements. To ensure user safety and product performance, the system has the capability to ensure that only authorized consumable solutions are used in the cleaning station. The RFID data capture capability, in conjunction with a video system, allows users to have real time feedback of their personal compliance as well as individual user focused information conveyed at the time of utilizing the cleaning station.

In accordance with one or more embodiments described herein, the user carries a RFID tag that is programmed with information specific to the individual. Upon approaching the cleaning station, an RFID reader recognizes the user's tag and records the user name, time, date, station location, and whether the cleaning event was a complete cycle. The data is stored in the readers' database until captured via various methods and transferred into a report format for the administrator. The administrator can then review the compliance statistics for the various users.

In a separate aspect of the invention, and in accordance with one or more embodiments described herein, the RFID system is well suited to monitoring whether a consumable item used in the cleaning station is authentic or not authorized. Upon detection of an improper consumables item the cleaning station may deactivate. An RFID tag is attached to the consumable product, such as a cleaning solution bottle. When installed in the cleaning station, the tag attached to the solution bottle will confirm to the RFID system by way of the unique tag identifier that the subject bottle contains an authorized solution. Without this verification, a user of the station may inadvertently use another solution that is harmful to the user or ineffective for the use intended. Another benefit is that an authorized solution will be at the correct viscosity to ensure the proper dosage is used in the wash cycle and the mechanical action of the station will not be compromised by plugged fluid nozzles and lines.

Embodiments of the present invention include methods of providing compliance or non-compliance information regarding hygiene efforts. By way of example and not limitation, a method for performing hygiene compliance verification is provided, comprising:

(a) receiving an object identifier;

(b) determining a cleaning protocol from a plurality of different protocols to be used on an object associated with the object identifier; and (c) implementing the cleaning protocol in connection with the object.

Other methods are also encompassed by the present invention. By way of example and not limitation, a method of performing hygiene compliance verification is provided, comprising: receiving hygiene compliance data associated with a plurality of enterprise networks, each network being associated with a different enterprise comprising one or more automated sensors; storing the hygiene compliance data; and providing at least one hygiene compliance data report, the hygiene compliance data report including hygiene compliance data received from a particular enterprise network of the plurality of enterprise networks.

Computer readable medium operable to perform the steps of any of the methods described herein are encompassed by the present invention.

Various signals, such as, by way of example and not limitation, a data signal associated with a carrier wave, that include at least one piece of hygiene compliance information are encompassed by the present invention. By way of example and not limitation, an electronic hygiene compliance verification data signal is provided, comprising:

(a) source and destination addresses;

(b) hygiene compliance information; and (c) an enterprise identifier; and (d) a compliance monitor identifier.

A variety of different ways of providing a compliance monitoring system are encompassed by the present invention. By way of example and not limitation, a compliance monitoring system is provided, comprising: means for receiving compliance data associated with a plurality of enterprise networks; means for storing the compliance data in a plurality of electronic storage locations, wherein each storage location corresponds to one enterprise network of the plurality of enterprise networks; and means for providing at least one compliance data report, the compliance data report including compliance data received from a particular enterprise network of the plurality of enterprise networks. Such system may further include means for providing the compliance data report to a web user, the web user having supplied a valid password. In addition, such system may further include means for providing the compliance data report to a compliance monitor.

In a hygiene compliance verification system, and by way of example and not limitation, a computer readable medium comprising a set of data structures is provided, the set of data structures comprising:

(a) a first set of information identifying a hygiene compliance monitor;

(b) compliance data required to be reported to the compliance monitor; and (c) reporting requirements associated with the compliance monitor;

wherein the data structures are used to produce a data management report including the compliance data. The set of data structures may further comprise a reporting frequency required by the compliance monitor. The set of data structures may further comprise location information, the location information identifying at least one of a geographical and geopolitical location monitored by the compliance monitor.

A variety of compliance monitoring systems are encompassed by the present invention. By way of example and not limitation, a compliance monitoring system for use with at least one hygiene station is provided, the system comprising:

(a) a verification module; and (b) an electronic storage location for storing compliance data collected by the at least one hygiene station, wherein the compliance data comprises a plurality of different object identifiers and different protocol identifiers, each protocol identifier being associated with a different cleaning protocol, wherein each object identifier has a corresponding protocol identifier and wherein at least one protocol identifier indicates that no cleaning be performed for the corresponding object identifier.

The system may further comprise a plurality of enterprise networks, each enterprise network including at least one corresponding hygiene station; and a plurality of electronic storage locations, each storage location being associated with a corresponding enterprise network and storing compliance data collected by the at least one corresponding hygiene station in the corresponding enterprise network.

Embodiments of the present invention cover compliance verification of different forms of a hygiene station. By way of example and not limitation, one or more embodiments of the present invention are appropriate for monitoring associated with hygiene stations that comprise a sink and a faucet, automated cleaning stations, disinfection stations, sanitizer dispensers, sanitizer gel dispensers, lotion dispensers, hand soap dispensers, or other ancillary devices, et cetera.

Other aspects of various embodiments not summarized here are also considered to form part of the present invention, either alone or in combination with other aspects. Accordingly, aspects may be claimed alone or in combination with other aspects.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic even if performance of the process or operation uses human input, whether material or immaterial, received before performance of the process or operation. Human input is deemed to be material if such input influences how the process or operation will be performed. Human input that consents to the performance of the process or operation is not deemed to be "material".

The terms "determine", "calculate" and "compute," and variations thereof, as used herein, are used interchangeably and include any type of methodology, process, mathematical operation or technique.

The term "module" as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 4 is an exemplary station-use record in accordance with embodiments of the present invention;

FIG. 5A is an exemplary employee record in accordance with embodiments of the present invention;

FIG. 5B shows a set of data structures according to an embodiment of the present invention;

FIG. 7 is an exemplary compliance report in accordance with embodiments of the present invention;

FIG. 10 is an exemplary data management module report;

FIG. 12 shows a set of data structures according to an embodiment of the present invention.

DETAILED DESCRIPTION

Figure 1:
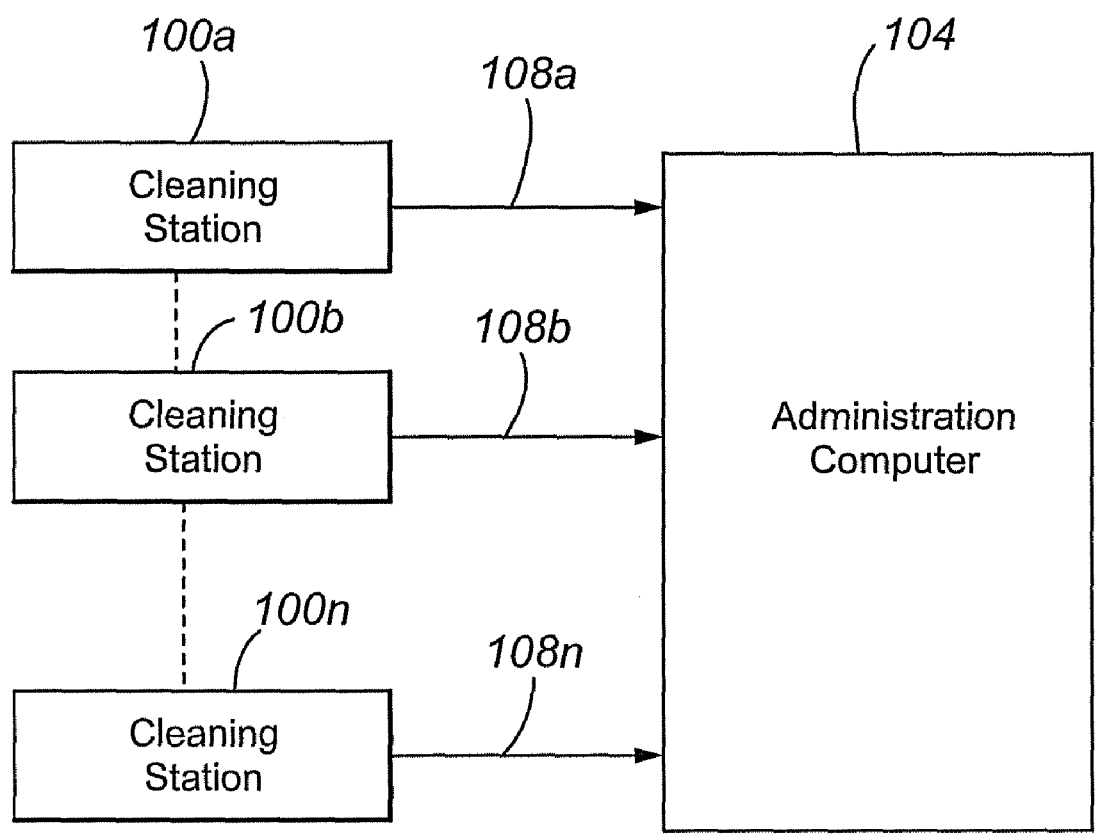
FIG. 1 is a block diagram of components that may be included in embodiments of the present invention.

The exemplary systems and methods of this invention will be described in relation to distributed processing networks. However, to avoid unnecessarily obscuring the present invention, the following description omits a number of known structures and devices. This omission is not to be construed as a limitation of the scope of the claimed invention. Specific details are set forth to provide an understanding of the present invention. It should, however, be appreciated that the present invention may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a washing station, or collocated on a particular node of a distributed network, such as an analog and/or digital telecommunications network, a packet-switched network, or a circuit-switched network. It will be appreciated from the following description, and for reasons of computational efficiency, that the components of the system can be arranged at any location within a distributed network of components without affecting the operation of the system. For example, the various components can be located in a switch, media server, gateway, in one or more washing stations, at one or more users' premises, or some combination thereof.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the invention.

The present invention is directed to a system and method for ensuring employee compliance with washing requirements, such as hand-washing requirements. However, it is to be understood that embodiments of the present application are also applicable to other types of washing systems, including for example, boot-washing systems. In accordance with embodiments of the present invention, employee use of one or more automated cleaning stations is monitored. The cleaning stations operate to dispense one or more fluids, such as water, a cleaning fluid, such as soap, and/or a disinfectant, etc., while a person's hands are placed in a washbasin. As used herein, a "washbasin" means a structure associated with the cleaning station where the hands (or boots) are cleaned, such as one or more wash cylinders, spray areas, pans, tubs, etc. Employees may be instructed to wash their hands for a minimum amount of time that has been determined to be sufficient to provide a complete cleaning. The minimum time needed to provide a complete cleaning and/or the types of fluids, agents, and/or cleaning methods used in the automated cleaning may vary depending a variety of factors including the employee's job duties and/or his or her past noncompliance. The cleaning stations are operable to record and report data related to employee compliance with such requirements. At least some employees may not be required to wash their hands.

For purposes of discussion, the various embodiments of the present invention are discussed herein in connection cleaning an appendage of a user. However, it should be understood that the various embodiments may be used in connection with other objects. As used herein an "object" may refer to anything cleaned by the automated cleaning station. An object may be, for example, an appendage of a user, a tool, a boot, and/or an inanimate object, etc. As used herein, "inanimate object" means an object that is principally not a biological tissue, although biological matter may be associated with the inanimate object, for example, a virus, bacteria, and/or pieces of tissue on a tool.

Referring now to FIG. 1, components of a compliance system in accordance with embodiments of the present invention are illustrated in block diagram form. Shown in FIG. 1 is a plurality of cleaning stations 100a, 100b . . . 100n. The cleaning stations 100a-100n may be used by people employed at a facility that requires employees to wash their hands. Such facilities may include, for example, restaurants, food processing facilities, hospitals and laboratories. Also shown in FIG. 1 is an administration computer 104 for use by a manager or administrator of the facility. The administration computer 104 is operable to generate a compliance report as described herein. As used herein, an administration computer 104 may include a file server or other network computer operable to serve as a data collection point for data associated with cleaning stations 100a . . . 100n. Additionally, it should be understood that separate computational devices may be used to store data and to access the stored data.

The administration computer 104 communicates with the cleaning stations 100a-100n over a plurality of communication links 108a, 108b . . . 108n. The communication links may be implemented by any one of a variety of methods and may depend on the type of facility in which the cleaning stations 100a-100n are used. In particular, the communication links 108a-108n may be implemented as part of a local area network (LAN) or a wide area network (WAN). As used herein, a "communication link" does not imply a direct connection between two endpoints. As can be appreciated by one of skill in the art, a "communication link" may include a communication session having parts that are routed through various nodes of a communication network. More particularly, the communication links 108a-108n may be implemented using such protocols as Ethernet or USB. The communications links 108a-108n may be implemented as wired or wireless connections. It may be the case that the administration computer 104 is located in a separate facility from one or more of the cleaning stations 100a-100n. In this case, a distributed data network such as the Internet may form part of the communication links 108a-108n.

Figure 2:
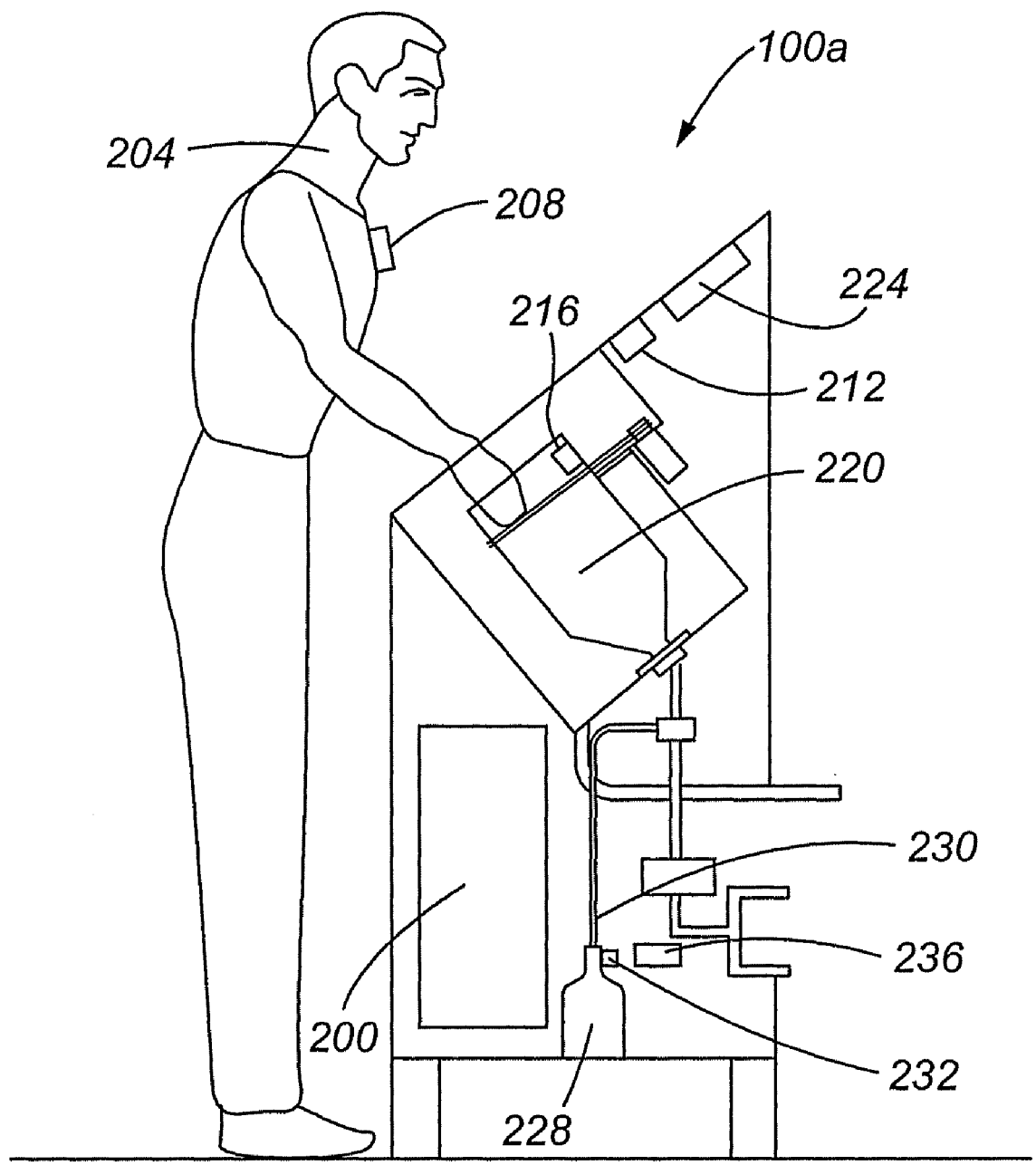
FIG. 2 is a schematic depiction of a cleaning station in accordance with embodiments of the present invention.

Referring now to FIG. 2, an exemplary cleaning station 100a is illustrated. The cleaning station 100a includes a cleaning station operations monitor 200. The cleaning station operations monitor 200 may comprise a computational device such as a general-purpose computer, controller, or ASIC that controls and coordinates the operation of the various electronic components associated with the cleaning station 100a. Additionally, the cleaning station operations monitor 200 is operable to record data associated with employee use of the cleaning station 100a and to report the data to the administration computer 104. The cleaning station operations monitor 200 may be incorporated into the cleaning station 100a or, alternatively, may be implemented as a separate computing device.

Also shown in FIG. 2 is a user 204 of the cleaning station 100a. The user 204 may be an employee or visitor who is required to wash their hands because of the nature of their work or the nature of the facility. The user 204 is shown wearing a user RFID tag 208. The user RFID tag 208 is programmed by an RFID tag programming device (not shown) with information such as an employee number that, when read, uniquely identifies the employee or user 204. The RFID tag 208 may be incorporated into an identification badge or bracelet worn by the user 204.

In accordance with embodiments of the present invention, the cleaning station 100a includes an RFID reader 212 and an optical sensor 216. The RFID reader 212 is positioned so as to be able to read the user RFID tag 208 when the user 204 is washing his or her hands at the cleaning station 100a. The RFID reader 212 may be incorporated into the cleaning station 100a or, alternatively, may be implemented as a stand-alone device. For example, the RFID reader 212 may be positioned adjacent to a cabinet associated with the cleaning station 100a. The optical sensor 216 is positioned so as to be able to sense that the hands of the user 204 are placed within the washbasin 220 in a position where they will properly receive cleaning fluids, such as water, soap and/or disinfectant as dispensed by the cleaning station 100a. The RFID reader 212 and the optical sensor 216 are in communication with cleaning station operations monitor 200, which, in turn, is operable to collect data associated with these devices. In particular, data is collected from the RFID reader 212 indicating the identity of the user 204. Additionally, the cleaning station operations monitor 200 records the length of time in which the hands of the user 204 were placed in the washbasin 220 as indicated by the optical sensor 216. In addition to RFID, other methods of identifying a user are within the scope of the present invention. In particular, a user may be identified by means of a typed password, retinal scan, voice print, palm print, fingerprint, face identification, bar coding (on an employee ID), etc.

The cleaning station 100a also includes a video display 224 positioned for viewing by the user 204 when he or she is washing his or her hands. The video display 224 may be incorporated in the cleaning station 100a or, alternatively, may be implemented as a separate device. For example, the video display 224 may be positioned on a wall in front of the user 204 as they stand at the cleaning station 100a. The video display 224 operates to display brief video segments to the user 204 while the cleaning station 100a is cleaning his or her hands. The video display 224 may be under the control of the cleaning station operations monitor 200. As the user 204 is utilizing the cleaning station 100a, administrator-selected data is transmitted to the video display 224. This information may be simple feedback to the user 204 informing them of the amount of hand washings they did in the current day, week, month, etc. In addition, there may be training programs that communicate information to the user 204, such as the risks of hand borne pathogens, to constantly remind the user 204 of the importance of hand hygiene. This system has the flexibility to provide a wide range of communications to the user 204.

Also shown in FIG. 2 is a consumables container 228 that contains a material, such as soap or disinfectant used in connection with the operation of the cleaning station 100a. Although not shown, a plurality of consumable containers 228 may be associated with a cleaning station 100a. The consumables container 228 includes a detachable connection to a consumable receptacle 230 associated with the cleaning station 100a so that the consumable container 228 may be removed and disposed of when its contents are expended. After the disposal of a used consumables container 228, a new consumables container 228 is then attached to the cleaning station 100a. In accordance with embodiments of the present invention, the consumables container 228 also includes a consumables RFID tag 232 that contains information related to the consumable container 228. A consumables RFID reader 236 associated with the cleaning station 100a reads the consumables RFID tag 232 and communicates information related to the consumables container 228 to the cleaning station operations monitor 200. Although RFID is discussed herein for use of identification of consumables, other types of identification systems may be used, such as bar codes.

Figure 3:
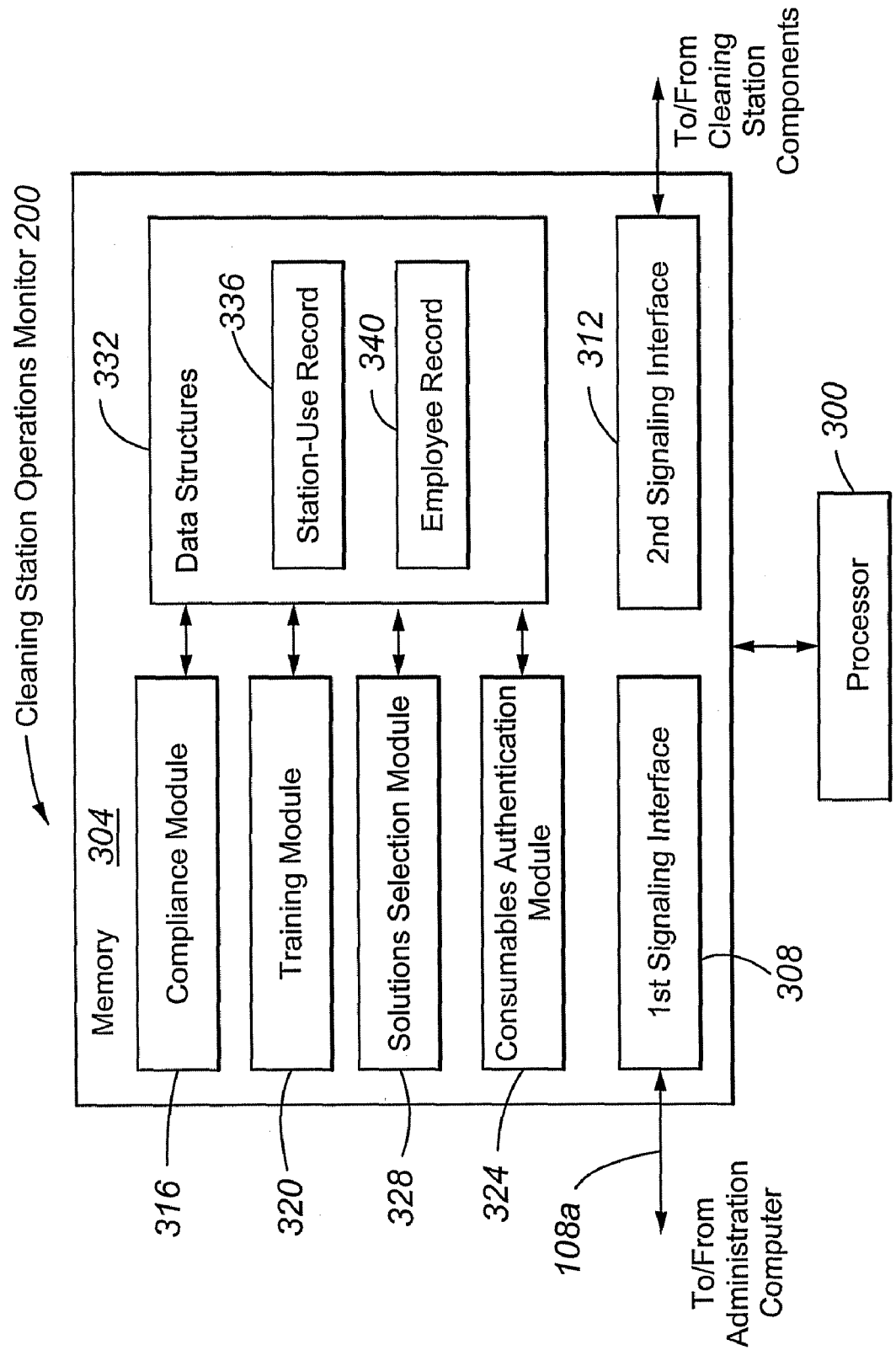
FIG. 3 is a block diagram of a cleaning station operations monitor in accordance with embodiments of the present invention.

Referring now to FIG. 3, a block diagram of components and features of the cleaning station operations monitor 200 is shown. As mentioned previously, the cleaning station monitor 200 is a computational device. Accordingly, the cleaning station operations monitor 200 includes a processor 300, a memory 304 and signaling interfaces 308 and 312 operable to communicate with external electronic and/or computational components. The first signaling interface 308 operates to communicate with the administration computer 104 over communication link 108a, as described above. The second signaling interface 312 operates to communicate with the various electronic components associated with the cleaning station 100a including the RFID readers 212 and 236, the optical sensor 216, and the video display 224. The second signaling interface 312 may be a portion of a backplane incorporated into cleaning station 100a that includes a connection to the cleaning station's 100a electronic components. Alternatively, if the cleaning station operations monitor 200 is implemented as a stand-alone computer, the cleaning station operations monitor 200 may communicate with the cleaning station's electronic components through a network or serial bus connection.

The memory 304 includes a plurality of stored program applications or modules that implement various features of a compliance monitoring system. In accordance with embodiments of the present invention, the memory 304 may include a compliance-monitoring module 316, a training module 320, a consumables authentication module 324, and/or a solutions selection module 328. Additionally, the memory 304 may include data structures 332 associated with the various modules. In accordance with embodiments of the present invention, the data structures 332 include a station-use record 336 and one or more employee records 340. The operation of the various modules and data structures is described in greater detail below.

The compliance-monitoring module 316 operates to monitor and record the activity of a plurality of users 204 of the cleaning station 100a. The process is outlined as follows. The user 204 approaches a cleaning station 100a with a RFID tag 208 on their person, which was programmed with a RFID tag programming device with the individual's name or number, and/or other pertinent data. The tag 208 is read by the RFID reader 212 when the user 204 approaches and/or begins using the cleaning station 100a. When the user 204 places his or her hands into the cleaning station washbasin 220, the optical sensor 216 initiates a cleaning cycle. If the hands of the user 204 do not stay in the washbasin 220 for the full cycle time, the optical sensor 216 will indicate in the data structure 332 that the user 204 did not have a complete cleaning. Once the user is finished using the cleaning station 100a, the data showing such items as user name, time, date, station location and/or identification, and whether the cycle was complete, etc., is stored in the data structure 332. The stored data is later accessed by the administration computer 104 in connection with the generation of a compliance report.

An exemplary station-use record 336 having data associated with a plurality of users 204 is shown in FIG. 4. In accordance with embodiments of the present invention, an entry in the station-use record 336 may include an employee name 400 indicating who used the cleaning station 100a, a time stamp 404 indicating when the cleaning cycle was initiated, a duration 408 indicating how long the user 204 kept his or her hands in the washbasin 220, the date 412, and a compliance indicator 416 specifying whether or not the user 204 kept his or her hands in the washbasin 220 for the required time. As an example, the station-use record shown in FIG. 4 indicates that on May 21, 2006 Janet Smith met the hand-washing requirement by completing a cleaning cycle that was initiated at 8:00.00 A.M. and that lasted for 10 seconds. In an alternative embodiment, the station-use record 336 may contain only raw data such as the time 404, date 412 and duration 408 of the cleaning cycle while determinations related to compliance requirements are made by a separate module running on the administration computer 104.

The compliance-monitoring module 316 may also operate to monitor hand-washing requirements that are specific to each employee. Some employees may have stricter hand washing requirements than others at the same facility. For example, a hospital emergency room may employ both surgeons and social workers. As can be appreciated, the surgeons will be required to wash their hands more frequently and more thoroughly than the social workers. Accordingly, the compliance-monitoring module 316 may access employee records to determine the type, concentration, and/or amount of cleaning fluid to be dispensed for a particular employee. Additionally, employee records may contain other hand washing compliance data that is specific to each employee such as the amount of time and/or frequency that an employee is required to wash his or her hands. Washing requirements may also depend on an employee's history of compliance with his or her washing requirements. For example, an employee may be required to wash his or her hands more thoroughly if his or her previous hand washings were incomplete or hand not been wash for some period of time.

Embodiments of the present invention may include a training module 320. In accordance with at least one embodiment of the present invention, the training module 320 operates to transmit educational information to the user 204 while the cleaning cycle is running via sound and/or a visual source, such as a video display 224. The information may comprise segments equal in duration, or slightly longer or shorter in duration than the cleaning cycle. For example, the segments may contain information regarding hand hygiene in a series of segments lasting approximately 10-15 seconds. In accordance with at least one embodiment of the present invention, the employee record 340 portion of the data structure 332 keeps track of the user 204 and knows the sequence of training segments so each time a user 204 uses the cleaning station 100a, the next pertinent training segment will display on the video display 224.

In accordance with at least one embodiment of the present invention, the training module 320 may access the employee record 340 to provide custom designed content in conjunction with the user's 204 needs/requests. Accordingly, as one possible alternative to educational/training content, entertainment content specific to the user's 204 preferences may be displayed. Here, other information is conveyed to the user, such as news (e.g., weather, breaking stories, current events, stock prices, etc.) and sports information. The training module 320 may, therefore, accommodate specific requests to convey information of interest to the user. In at least one embodiment of the present invention, the information conveyed to the user may be anything other than information about a cleaning station function parameter (e.g., water pressure, soap level, etc.). That is, content other than information about the cleaning station operating parameters so that the user is interested in staying at the cleaning station for an entire wash cycle.

The training module 320 may give feedback to the user 204 through the video display 224, including such information as their hand-washing statistics over a given period of time. For example the administrator of a facility may want to encourage system usage by conveying one or more compliance statistics, and/or informing a user 204 that the user 204 has won a prize by having high marks for compliance with the hand-washing protocol. Accordingly, the employee record 340 may keep track of data associated with user 204, and this data may be accessed by the training module 320 to inform the user 204 in real time, and/or the administrator in a subsequent report, as to compliance statistics. Additionally, the video display 224 may be used to provide notices, such as for upcoming meetings and events that are pertinent to all staff or to a specific person.

The solutions selection module 328 may determine which solution is to be used with each individual user 204. For example, one user 204 may have an allergy to the standard solution, so the system is programmed to automatically use a different and appropriate solution when this user 204 is identified through their RFID tag 208. Information related to user allergies may be contained in the employee record 340.

An exemplary employee record 340 for use in connection with both the training module 320 and the solutions selection module 328 is shown in FIG. 5A. In accordance with embodiments of the present invention, an entry in the employee record 340 may include the employee name 500, hand-washing 504 statistics associated with employee, current training segment 508 to be viewed by the employee, the employee's preferred entertainment content 512, and/or a listing of the employee's allergies 516. As an example, the employee record shown in FIG. 5A indicates that Bill Forbes is in 97% compliance with the hand-washing requirement, has currently viewed seven training modules, prefers to watch the news while washing his hands, and has an allergy to cleaning solution A.

In accordance with embodiments of the present invention, an employee record may include a lookup table that indicates a particular cleaning protocol that is to be applied to a particular employee. An exemplary lookup table 520 is shown in FIG. 5B. The lookup table 520 includes a plurality of employee identifiers 524 and, for each employee identifier, a corresponding employee type indicator 528 and cleaning protocol identifier 532. The employee identifier 524 is commonly an RFID or suitable wirelessly readable identification code. The employee type indicator 528 commonly references the job responsibilities and/or title/position of the identified employee. For example, in a caregiver application a "1" might refer to a nurse, a "2" to an imaging technician, a "3" to a doctor, and a "4" to a member of the janitorial staff. Alternatively or in combination, the particular individuals may be identified by a key code including a name or a job description. The cleaning protocol identifier 532 refers to the particular cleaning protocol to be used for the corresponding identified employee. Typically, each cleaning protocol has a corresponding set of cleaning medium to be used, medium application duration, and wash duration. For example, cleaning protocol identifier "1" may require a ChlorHexidine Gluconate ("CHG") wash, a "2" either a CHG wash or alcohol towelette or wipe, and a "3" a CHG wash followed by an alcohol wipe. Examples of other sanitizing solutions that may be used individually or collectively in cleaning protocol(s) include quaternary ammonium solutions. In one configuration, the cleaning protocol identifier is further varied based upon the location of the corresponding washing station, which is readily determined from the station identifier. A washing station in a highly hygiene sensitive area, such as an operating room, may provide a more demanding cleaning protocol than a station at a less hygiene sensitive area, such as a nursing station. In some cases, the cleaning protocol identifier may indicate that no cleaning is required. For example, the data structures of FIG. 5B show that, for employee type "4", the protocol identifier has a value of "0", or no cleaning is required.

It should be understood that the data fields associated with the exemplary employee record 340 discussed above and shown in FIG. 5A and the lookup table 520 shown in FIG. 5B are by way of illustration and not limitation. A particular employee record 340 may include other fields such as, for example, a user's department, an auto-assigned system identification number, a RFID number, a user identification number, one or more contact telephone numbers, and/or a contact email address. As can be appreciated, the choice of data fields used in a particular employee record 340 will vary depending on the context and the requirements that are particular to each use of the present invention.

In accordance with embodiments of the present invention, the employee record 340 may be an instance of a global employee record maintained centrally at the administration computer 104. Accordingly, the administration computer may periodically access and/or update a plurality of instances of employee records 340 associated with each cleaning station 100a-100n in order to maintain a comprehensive employee record. Alternatively, at least a portion of the employee use record 340 or data described herein as being associated with the employee use record 340 may be stored in the RFID tag 208 worn by the user 204. For example, a list of the user's 204 allergies may be stored in his or her RFID tag 208 and read by the RFID reader 212 when the user 204 washes his or her hands.

Embodiments of the present invention may include operation of a consumables authentication module 324 that operates to recognize when a non-authorized solution is introduced into the system. The consumables container 228 and/or a receptacle or fitting associated with the cleaning station 100a for receiving the consumables container 228 may be mechanically designed to discourage introducing non-authorized solutions to the system. In accordance with embodiments of the present invention, the consumables container 228 includes a consumable container RFID tag 232 that is recognized by the RFID reader 236 as an approved solutions container. If the consumables container 228 is withdrawn from the cleaning station 100a and reinstalled, the RFID reader 236 will recognize the tag as invalid and warn the user 204 through the video display 224 and/or the administrator through the administration computer 104 that this is not acceptable and potentially void the product warranty. Alternatively, or in addition thereto, an option is available where the cleaning station 100a will stop functioning at the direction of the consumables authentication module 328 until a proper consumables container 228 with a valid RFID tag 232 is inserted into the cleaning station solution receptacle 230. In yet another possible alternative and/or in addition to the options provided above, the known number of doses or applications of the consumable material may be associated with a valid RFID tag 232 and monitored by the consumables authentication module 328 so that once the number of applications is reached (and thus the consumable expended) the cleaning station 100a cannot be used until another valid consumables container 228 is installed. For example, say that one consumables container 228 contains enough cleaning fluid for approximately 500 hand-washing cycles. Once the cleaning station 100a has administered approximately 500 hand-washing cycles using a particular consumables container 228, then this container will no longer be operable with the cleaning station 100a. This prevents the consumable container 228 from being removed, refilled with a non-approved cleaning fluid, and then reattached for use with the cleaning station 100a. Such forced compliance for use of the proper consumables provides compliance regulators and/or administrators confidence that, for example, the approved disinfectants are being applied to the users 204 hands with each cleaning or use.

In addition to RFID, other methods and/or systems may be used to identify the consumables container 228. In particular, the consumable container 228 may be identified by a bar code and bar code reader. Moreover, the present invention may include modules that perform other functions such as collecting and reporting maintenance data; reporting information on the last recorded information transfer; and/or reporting the cleaning station's name, type, IP address and current software version.

Figure 6:
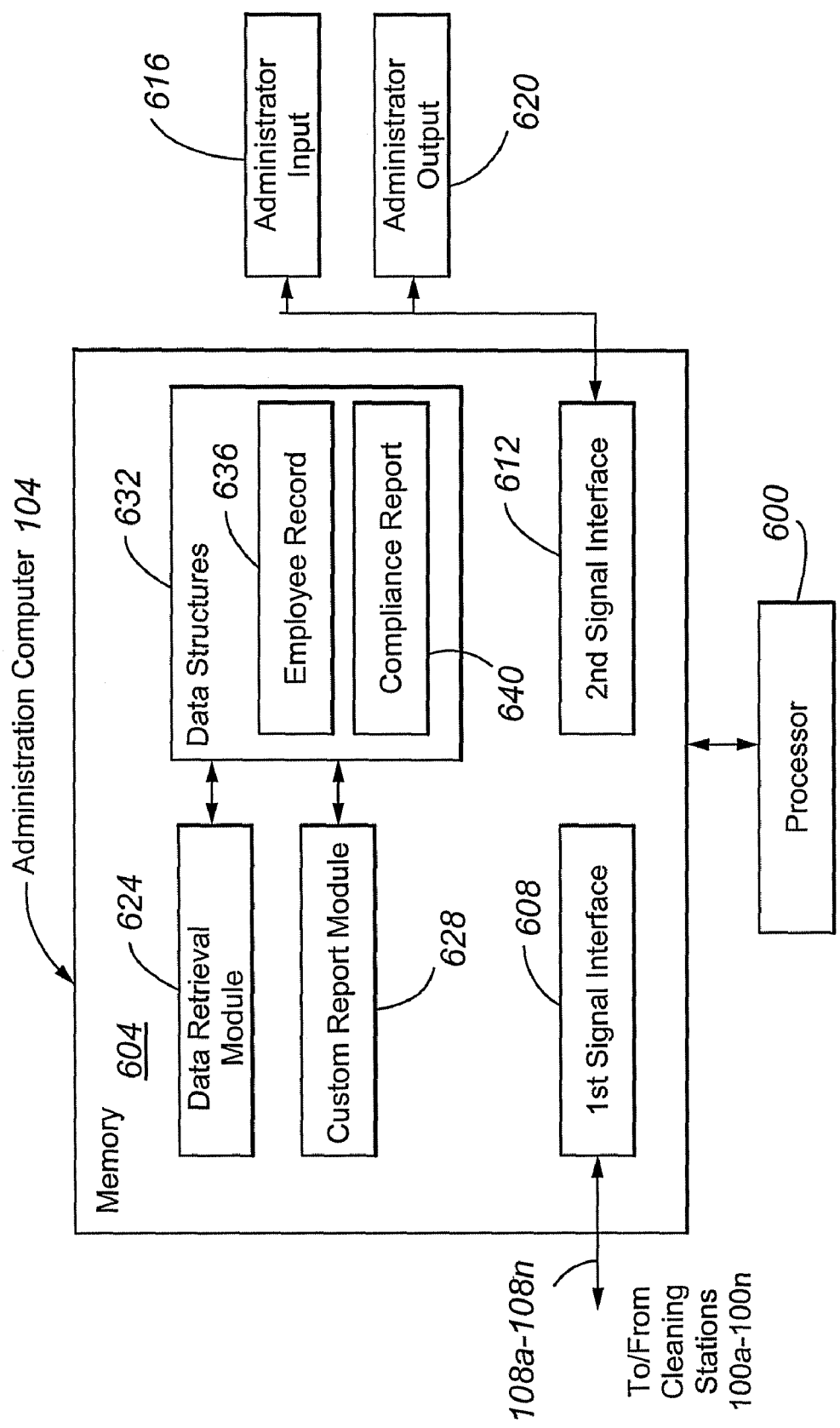
FIG. 6 is a block diagram of an administration computer in accordance with embodiments of the present invention.

Referring now to FIG. 6, a block diagram showing components and features of the administration computer 104 is illustrated. Administration computer 104 includes a processor 600, a memory 604 and signaling interfaces 608 and 612 operable to communicate with external electronic and/or computational components. The first signaling interface 608 operates to communicate with the cleaning stations 100a-100n over communication links 108a-108n, as described above. The second signaling interface operates to communicate with the various input 616 and output 620 devices associated with the administration computer 104. The input device 616 may be, for example, a keyboard or a mouse. The output device 620 may be, for example, a monitor or a printer.

The memory 604 includes a plurality of stored program applications or modules that implement various features of a compliance monitoring system. In accordance with embodiments of the present invention, the memory 604 may include a data retrieval module 624 and a custom report module 628. Additionally, the memory 604 may include data structures 632 associated with the various modules. In accordance with embodiments of the present invention, the data structures 632 may include an employee record 636 and/or a compliance report 640. As can be appreciated by one of skill in the art from the disclosure herein, the memory 604 may include database structures implemented using suitable database software (such as SQL Server Express).

The data retrieval module 624 operates to retrieve data associated with cleaning stations 100a-100n. Such data may include data related to cleaning station usage and/or employee specific data. The data may be contained in a cleaning station-use record 336 and/or an employee record 340 associated with a cleaning station 100a-100n. Additionally, the data retrieval module 624 may operate to maintain a global employee record 636 as described above.

The custom report module 628 operates to generate the compliance report 640. The compliance report is generated from data contained in each station-use record 336 associated with cleaning stations 100a-100n. An exemplary compliance report is shown in FIG. 7. In accordance with embodiments of the present invention, an entry in the compliance report 640 may include an employee name 700, time stamp 704 indicating when a cleaning cycle was initiated, the date 708 of the cleaning cycle, the location 712 where the cleaning cycle took place, and a compliance indicator 716 specifying whether or not the user 204 met the compliance requirement. As an example, the compliance report shown in FIG. 7 indicates that on May 21, 2006 Janet Smith met the hand-washing requirement by completing a cleaning cycle that was initiated at 8:00.00 A.M at cleaning station A. As noted, compliance reports may include data pertaining to user statistics. Alternatively, or in addition to reports comprising user statistics, reports may be generated that are directed to the consumables, such as soap and disinfectants.

The compliance report 640 may be generated at different time intervals and may be grouped based on different criteria. For example, the compliance report may be generated daily, weekly, monthly, yearly, et cetera. Moreover, the compliance report 640 may be generated that are grouped by individual or station.

Figure 8:
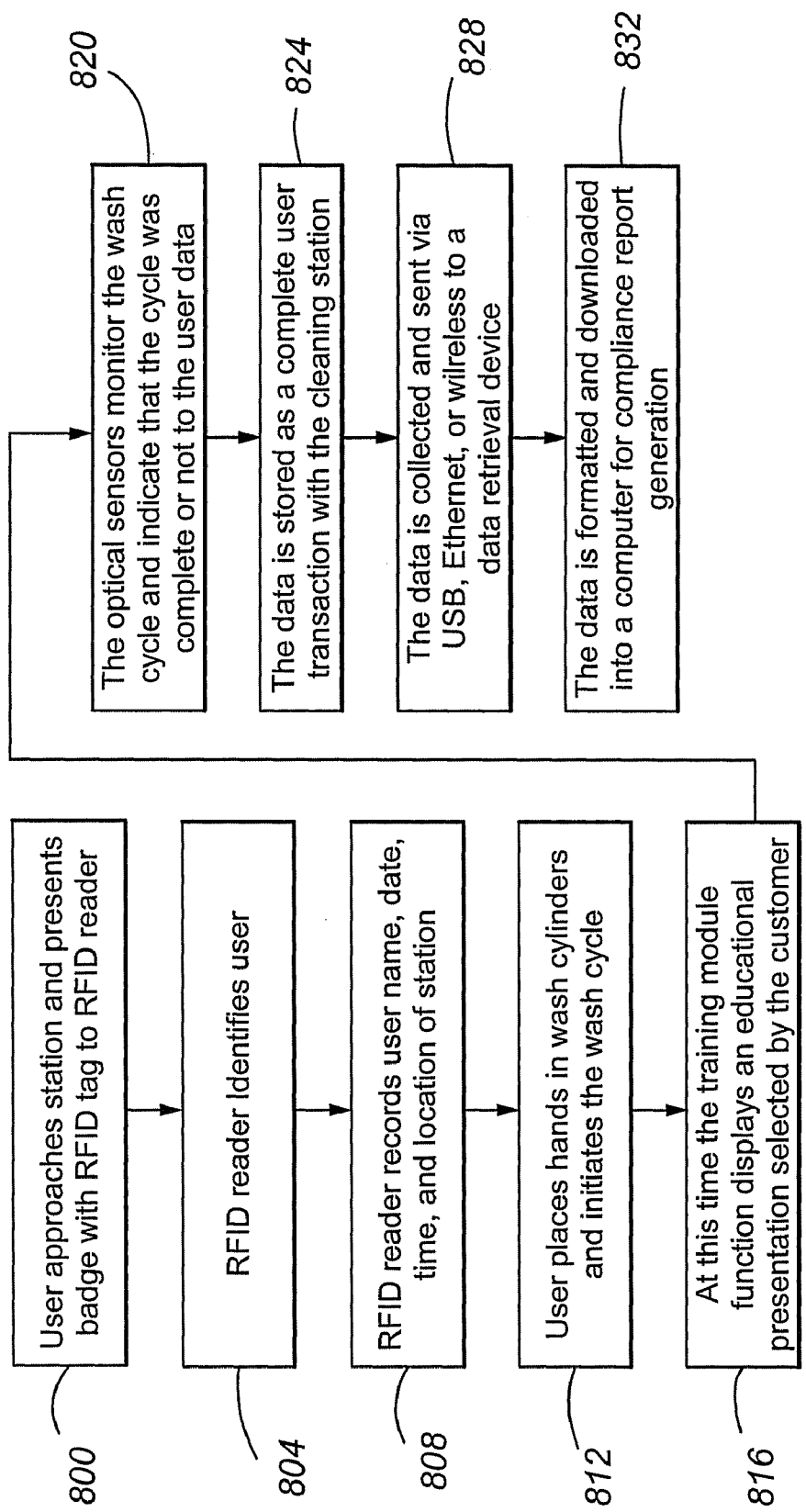
FIG. 8 is a flow chart depicting aspects of a method of monitoring hand-washing compliance in accordance with embodiments of the present invention.

In accordance with embodiments of the present invention, FIG. 8 shows a block diagram illustrating the steps of a method of monitoring a compliance requirement. Initially, at step 800 a user 204 approaches a cleaning station 100a and presents a badge having a RFID tag 208 to an RFID reader 212. At step 804 the RFID tag 208 is read and the user 204 is identified. At step 808 the user's 204 name, the date, the time, and the location of the cleaning station 100a are recorded. At step 812 a cleaning cycle is initiated when the user 204 places her or his hands in position to be washed. During the wash cycle, at optional step 816, the user 204 is provided with educational or entertainment content through the video display 224. At step 820 the wash cycle is completed and data is recorded including the duration of time the user 204 allowed his or her hands to be washed. At step 824 the transaction is completed and recorded. At step 828, data is collected from the cleaning stations 100a-100n over the communication links 108a-108n. In particular, data may be routed to a central collection point or FTP folder. Finally, at step 832, the collected data is used to generate a compliance report 640. Additional steps associated with the method may include: monitoring proper use of consumables; warning that an improper consumables container 228 has been installed; warning that a consumables container 228 is empty or nearly empty based on the number of uses since being installed; and warning that none or more users are failing to meet compliance requirements.

Figure 9A:
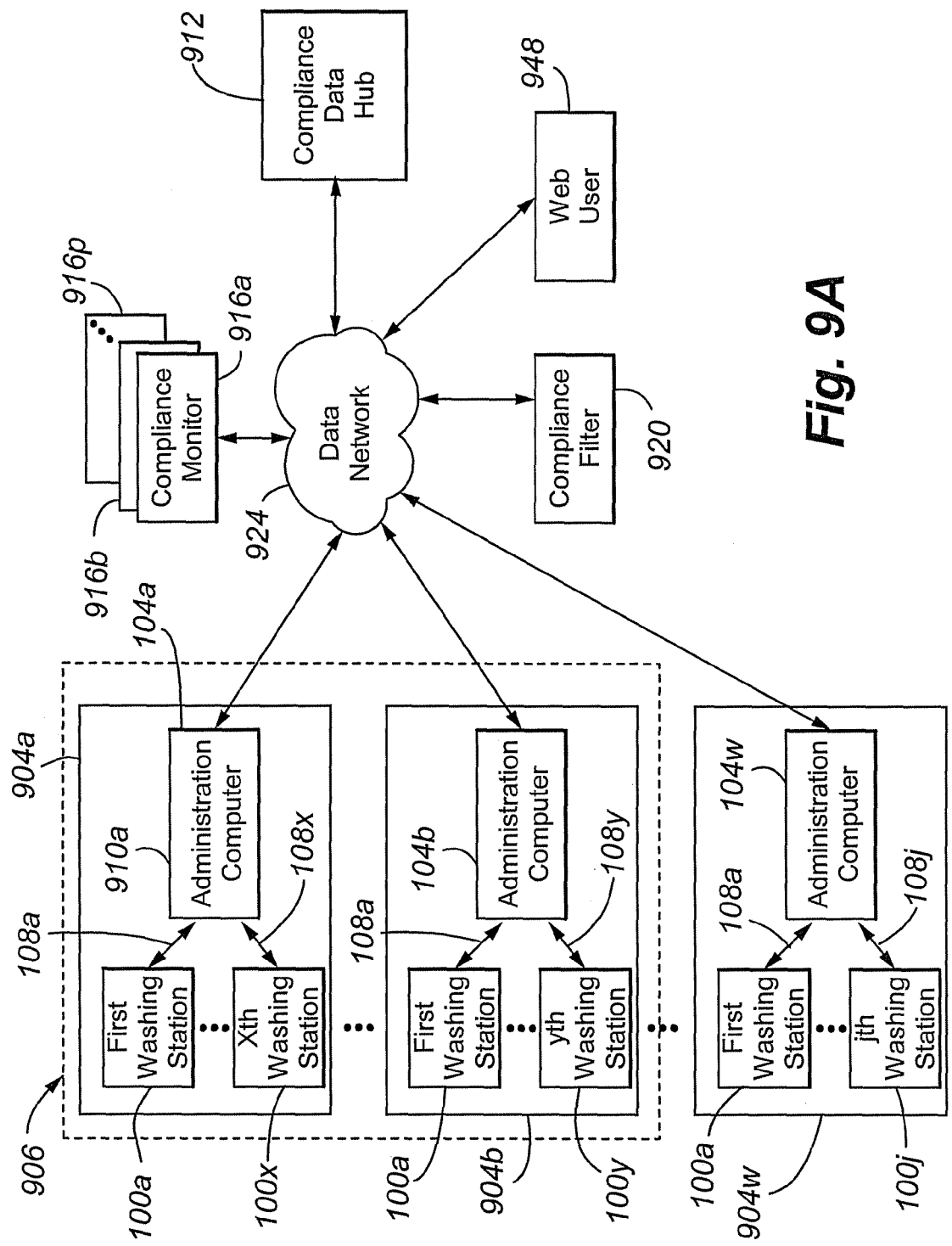
FIGS. 9A and 9B are a compliance monitoring system according to another embodiment of the present invention.
Figure 9B:
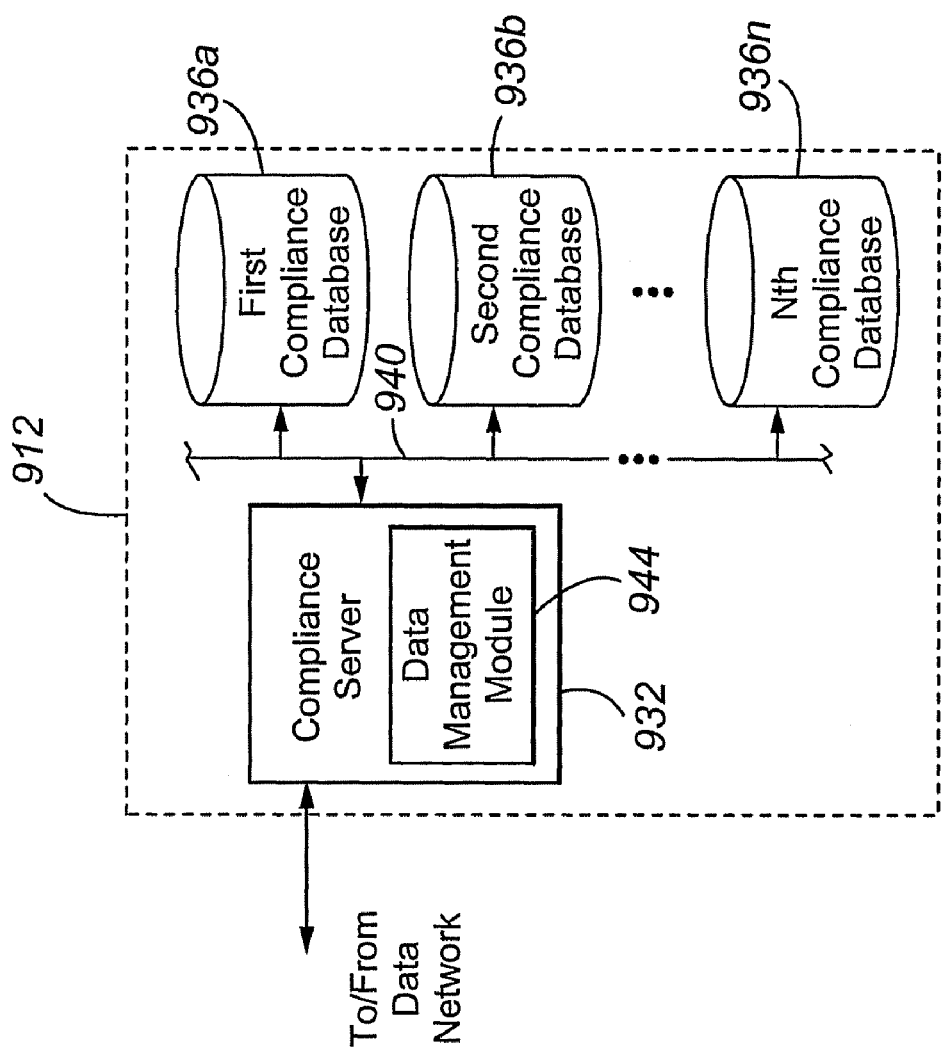

In another embodiment, a web-enabled hygiene monitoring system is provided. As shown in FIGS. 9A-B, the system 900 includes a plurality of discrete monitored entities 904a, b-w, each comprising first, second, . . . xth; first, second, . . . yth; or first, second, . . . jth washing stations 100a-x, 100a-y or 100a-j, respectively, a compliance data hub 912, a compliance monitor 916a,b-p, and a compliance filter 920, all interconnected by a data network 924.

The entities 904a,b-w are each a monitored location. Particular monitored entities may be discrete facilities of a common monitored enterprise. For example, the compliance data hub 912 may monitor a network of hospitals or restaurants. Referring to FIG. 9A, the monitored entities 904a and 904b represent different locations associated with a common business enterprise 906. Alternatively, a monitored enterprise may include only one monitored entity. In FIG. 9A, monitored entity 904w represents a separate business enterprise. In other words, the compliance data hub 912 may be associated with a plurality of business enterprises that are owned and operated by different companies, and one or more of those enterprises may include a plurality of different locations or facilities. Examples of enterprises include health care providers, food service providers (e.g., restaurants), food and/or drink manufacturers (e.g., meat packing plants, dairy product manufacturers, and the like), and other types of providers subject to internal and/or regulatory cleaning requirements.

In accordance with embodiments of the present invention, each monitored entity 904 network includes an administration computer 104a,b-w or data collection point that collects cleaning information from each washing station 100a-x, a-y, a-j in the corresponding enterprise network and, periodically or continually, provides the information to the compliance server 932 (shown in FIG. 9B) of the compliance data hub 912. As can be appreciated, an administration computer may be a network computer or server and may include a database. In this configuration, the cleaning information may be pushed by the administration computer 104*a,b-w* to the compliance server 932 or pulled from the administration computer 104*a, b-w* by the compliance server 932. Furthermore, it is noted that configuration of the each monitored entity 904*a,b-w* substantially corresponds to the embodiment of the present invention shown in FIG. 1.

Each administration computer 104*a,b-w* may include a user interface through which employee related data may be entered. The user interface may be implemented using any suitable software package (such as Access 2003) and can include portions that are icon driven to facilitate data entry and include drop down menus to ensure consistency of data. Additionally, data may be dynamically saved when possible. The user interface may include a plurality of screens wherein data is saved after a screen is changed. When changing screens, a user may be prompted to enter data not previously saved. Moreover, mandatory data fields may be supported for a software versions.

The washing stations 100*a-x, a-y, a-j* can be any type of cleaning equipment and are typically at different spatial locations in the monitored entity. Examples of washing stations include manual and automated body member (e.g., hand, foot, etc.) and other object washing stations, such as automated hand washers, sinks/faucets and cleaning solution dispensers, and the like. As will be appreciated, "object" refers to living or animate organisms, such as people and animals, as well as inanimate objects or entities, such as equipment and tools.

As discussed below, each monitored entity 904*a, b-w* has a corresponding unique monitored entity identifier, and, within each monitored entity 904*a, b-w*, each washing station 100*a-x, a-y, a-j* has a unique station identifier. Accordingly, each pairing of monitored entity and station identifiers is unique. In one configuration, an object type identifier (not shown) is used in addition to the employee type identifier. The object type identifier refers to animate and inanimate objects, each of which has a unique or substantially unique identifier. While the identifier is carried removably by persons, the identifier may be attached permanently or semi-permanently to the inanimate object. The identifier can be, for example, a passive RFID tag, a bar code label, and the like. Unlike employee identifiers, which, for an enterprise, are unique, inanimate object identifiers may not be unique for each individual object in the enterprise but unique for a class of objects of the same type. Thus, objects of the same type have a common identifier, while objects of different types have different identifiers.

Each washing station 100*a-x, a-y, a-j* includes a compliance module 316 that in turn includes a processor and computer readable storage medium. The compliance module 316 identifies objects to be cleaned, determines a suitable cleaning protocol for the object to be cleaned, records object identifiers, object type identifiers, cleaning protocol identifiers, timestamps, compliance indicators, alert instances, and the like, determines the compliance or noncompliance of a cleaning, and generates appropriate alerts. Additionally, each washing station 100*a-x, a-y, a-j* can further include modules to determine whether the operational status of the corresponding washing station or a component thereof. As noted, the operational status includes not only whether the washing station or a component thereof is fully or partly operational or nonoperational, but also quantitatively a current level or remaining amount of a consumable item, such as soap or a cleaning/antimicrobial solution, or qualitatively whether the consumable level falls below a threshold level. Each module 316 may be associated with a memory 304 that typically includes a record or lookup table listing, by employee identifier, a corresponding cleaning protocol identifier.

The compliance data hub 912 generally collects, stores, and analyzes cleaning information from the various administration computers 104*a, b-w*. (The administration computers 104*a, b-w* having collected hand-washing data from the individual cleaning stations 100*a-x, a-y, a-j*.) The compliance data hub 912 includes a compliance server 932 for receiving cleaning information and forwarding the cleaning information to an appropriate storage location in the compliance data hub 912, and for retrieving requested cleaning information from an appropriate storage location and forwarding the information to an authorized and verified entity, such as compliance monitor 916*a, b-p*. In that regard, the compliance data hub 912 further includes one or more databases 936*a-n* for storing cleaning information and a Local Area Network 940 interconnecting the databases with the server 932. The databases 936*a-n* may be separate, as shown, with each database corresponding to a monitored entity 904*a-n* or a single database partitioned into segments, one segment for each monitored entity 904. The databases 936*a-n* may be implemented using suitable database software (such as SQL Server Express).

The various administration computers 104*a, b-w* associated with the various monitored entities may support modules that communicate with compliance data hub 912. In accordance with embodiments of the present invention, it may by necessary to import a license token from the compliance data hub 912 in order to enable modules used at the administration computer level. The token may be specific to a particular enterprise and may include: the company name, a primary contact and primary contact information, a secondary contact and secondary contact information, the number of licensed users, and the type of service supported. In accordance with embodiments of the present invention, the token may be an encrypted string of text that will be delivered as a token license file. Moreover, the compliance data hub 912 may periodically access and/or update modules at the administration computer level. In accordance with embodiments of the present invention, an email may be generated providing notice that a particular module was accessed or updated.

As shown in FIG. 9B, the compliance server 932 includes a data management module 944 that queries administration computers 104*a,b-w* for cleaning information, forwards received cleaning information to an appropriate database 936 for storage, receives requests for cleaning information and, after successful authentication and verification of the request source, retrieves and forwards the requested cleaning information to the requesting source, and analyzes the cleaning information for instances of compliance and/or noncompliance events.

The data management module 944 is operable to provide a data management module report. An exemplary data management module report 1000 is shown in FIG. 10. The data management module report 1000 may include an enterprise identification number 1004. The compliance data hub 912 may assign a unique enterprise identification number 1004 to each business enterprise monitored by the compliance data hub 912. For example, the enterprise identification number 1004 having a value "123456", as shown in FIG. 10, may be associated with the business enterprise 906 shown in FIG. 9A. A particular compliance data report 1000 may be provided in connection with a particular business enterprise and will typically not include compliance data associated with other entities monitored by the compliance data hub 912. In particular, monitored entity 904*w*, which is not part of business enterprise 906, would be associated with a different enterprise identification number 1004. Accordingly, compliance data associated with the monitored entity 904w would not appear on the exemplary compliance data module report shown in FIG. 10. The data hub 912 may maintain a contacts module operable to store and track contact information associated with each monitored business enterprise.

The data management module report 1000 may additionally include a station identification number 1008 and a user identification number 1012. For a particular entry in the report 1000, the station identification number 1008 indicates the particular washing station where the washing took place. The user identification number 1012 is associated with a particular individual, such as an employee. Accordingly, for a particular entry in the report the user identification number indicates who used the washing station. Each entry in the report 1000 includes a date 1016 and time 1020 indication when the washing took place. A facility identifier 1024 may also be included if the monitored enterprise associated with the report 1000 includes more than one location or facility. The facility identifier 1024 may indicate in which facility within a particular enterprise the washing took place. The report also includes an indication 1028 of whether or not a complete wash cycle wash performed.

Additionally, the data management module report 1000 may include a compliance monitor identification number 1032. The compliance monitor identification number 1032 may be used to indicate which compliance monitor 916a, b-p of a plurality of compliance monitors 916a, b-p is currently receiving or will be receiving compliance data associated with a particular item in the data management module report 100. In addition or in the alternative, the compliance monitor identification number 1032 may be used by the compliance filter 920 in connection with determining which data items in the data management module report will be sent to the compliance monitors 916a, b-p. It should be appreciated that a particular report may include other fields not shown in FIG. 10. For instance, the report may include a wash station name or a wash station IP address.

Data management module reports 1000 may be generated at different time intervals and may be grouped based on different criteria. For example, reports 1000 may be generated daily, weekly, monthly, yearly, et cetera. Moreover, reports 1000 may be generated that are grouped by individual, company, facility, station, et cetera.

The compliance hub 912 may allow particular individuals to access stored data and/or reports including the data management module report 1000. In accordance with embodiments of the present invention, a report 1000 may be accessed remotely through a web interface. In that regard, web user 948, with proper access permission, can access compliance data stored in the compliance data hub 912. Particular individuals given access to stored data may include, for example, company managers and/or officers. As described in greater detail below, a report may be provided to a compliance monitor 916a, b-p.

Access to data management module reports 1000 and other stored data may be limited and/or controlled by a security system. In that regard, the data compliance hub 912 may include a group security module that provides a password protected control to stored data. The level of access allowed to a particular individual may be based on their membership in a particular group. Particular groups can include, for example, account manager, customer, demo, administration, data hub administration, and developer. Particular functions such as view, store and print may be useable based on the level of access granted.

The compliance data hub 912 can perform a variety of data processing functions. The compliance data hub 932, for example, can compare cleaning information, or a given sensed parameter, to identify events, temporal trends, or differences and, if necessary, generate appropriate alarms. The alarms can be logged internally and/or forwarded to the respective cleaning station 100a-x, a-y, a-j. The cleaning station 100a-x, a-y, a-j can then provide the alarm or warning to the appropriate cleaned object that, for instance, the cleaning provided was not compliant. An exemplary alarm may be "Successful Cleaning", "Warning Cleaning Failed", and the like. In another configuration, the alarm is that a consumable level is low and requires replacement or that the wrong consumable is being used. The compliance data hub 912 can also provide communications to the cleaning stations. The communications can, for example, be audio and video information for display to users of the stations. As will be appreciated, the audio and video information may be streaming media transmitted over the data network 924, including, but not limited to, video transmitted to video display 224.

In one configuration, the databases 936 further include, or reference, information collected and stored by the enterprise security system (not shown). For example, employee badge activated entrances typically collect the badge identifier (or employee identifier) and a timestamp when the badge identifier was received. Such information can be used in analyzing compliance by determining whether the employer having the sensed badge identifier used the washing station in temporal proximity to passing through the secured entrance. As will be appreciated, the spatial locations of activated entrances and washing stations are known and can be used, collectively, to monitor compliance.

The one or more compliance monitors 916a, b-p may be, for example, an entity responsible for monitoring and/or otherwise administering the hygiene policies and/or requirements of the one or more enterprises associated with the monitored entities 904. The monitor may be a governmental entity, such as a department of health and human services and the U.S. Food and Drug Administration, to name but a few, or a private entity such as a hygiene administration department. Typically, a plurality of compliance monitors 916a, b-p are involved, with each monitor being associated with a different local, state, or national (federal) government entity. By way of example, a facility of an enterprise 906 may need to report compliance data to multiple compliance monitors 916a, b-p, such as at the city or municipality, county, state, and federal levels.

In one or more embodiments of the present invention, a compliance filter 920 may be used. The compliance filter 920, in one configuration, receives outgoing transmissions of cleaning information and filters the information before it is provided to one or more of the compliance monitors 916a, b-p. The compliance filter 920 may be part of or separate from (as shown) the compliance data hub 912. The compliance filter 920 ensures that cleaning information from different monitored enterprises 906 is not intermixed and only necessary cleaning information is provided to the compliance monitor 916a, b-p, thereby protecting client/customer confidentiality and legally recognized privileges. In one configuration, the compliance filter 920 is a law firm responsible for and knowledgeable about compliance monitoring requirements. Attorneys may review the cleaning information and maintain the confidentiality of the cleaning information under the attorney-client privilege. Furthermore, in at least one embodiment, the compliance filter 920 is an auditing entity other than a law firm.

The data network 924 can be any circuit- or packet-switched network, with a packet-switched network, such as the Internet or World Wide Web, being preferred.

The cleaning information is typically converted into a selected form, packetized, and transmitted over the network 924. The form of the information can be in accordance with any selected language, such as the eXtensible Markup Language or XML, the HyperText Markup Language or HTML, Remote Method Invocation or RMI, or Direct Socket Connections. The packets can be transported using any suitable protocol, such as the Transport Control Protocol/Internet Protocol suite of protocols, Simple Object Access Protocol, or User Datagram Protocol.

Figure 11:
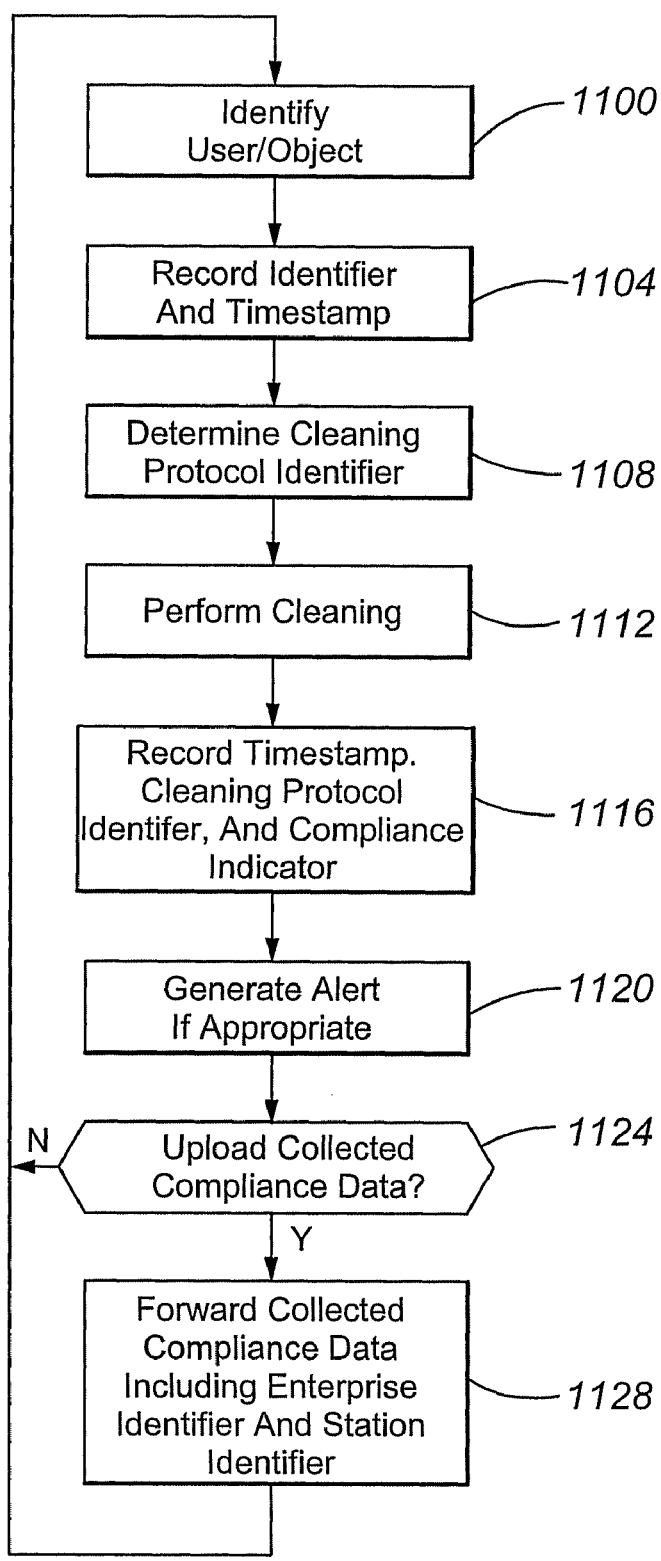
FIG. 11 is a flow chart according to an embodiment of the present invention.

The operation of the hygiene monitoring system will now be discussed with reference to FIG. 11.

In step 1100, the compliance module 316 of a selected washing station 100 identifies an object within range of the sensor. For example, an RFID tag identifier code associated with an animate or inanimate object is read by the RFID reader. Control then passes to step 1104.

In step 1104, the sensed identifier code and a first timestamp are recorded by the module 316. The first timestamp is indicative of the start time of the cleaning or washing cycle. In other configurations, the actual time that the cleaning cycle is commenced is sensed by a suitable sensor, such as an infrared sensor, motion sensor, or other type of optical or electromagnetic sensor, and recorded.

In step 1108, the module 316 maps the sensed identifier code against the lookup table of FIG. 5B and determines, for the sensed identifier code, a corresponding value for the cleaning protocol to be employed. The module 316 then configures the corresponding washing station 100 for performing the cleaning steps required by the protocol.

In step 1112, under the control of the module 316 the washing station 100 cleans the identified object according to the requirements of the cleaning protocol. In one configuration, the washing station 100 provides audible or visual instructions to the identified object or to an operator cleaning the identified object regarding the protocol requirements and senses when the various protocol steps are performed.

In step 1116, the module 316 records the sensed identifier and a second timestamp when one or more steps of the cleaning protocol is/are completed or, if the cleaning protocol steps are not completed, when the object to be cleaned is no longer within range of a sensor (e.g., the RFID reader or infrared sensor) of the washing station 100. The module 316 further records, for the sensed identifier, the protocol identifier for the corresponding protocol, and a compliance indicator (e.g., whether the protocol was successfully or unsuccessfully completed before the sensed identifier left sensor range).

In step 1120, an appropriate alert is generated depending on whether the protocol was successfully or unsuccessfully completed. The alert or warning can be provided to the object by the washing station 100.

In decision diamond 1124, the module 316 determines whether collected compliance data or cleaning information should be uploaded to the data network 924 for transmission to the compliance server 932. The trigger for uploading the information could be, for example, time-based, based on the number of washings performed by the corresponding station, or based on the available or unavailable memory capacity of the module 316 in the corresponding station. Alternatively, the trigger could be the receipt of a request from the server 932 for the information.

When the collected compliance data is to be provided to the server 932, the module 316 generates one or more signals containing the data and includes, in each signal, the monitored entity identifier of the corresponding monitored entity (e.g., the identifier of the enterprise operating the washing station 100) and station identifier of the washing station 100 performing the cleaning. As noted, the monitored entity identifier is unique among the monitored entities, and the station identifier among the various stations 100 operated by the corresponding monitored entity. The signal(s) are then forwarded to the compliance server 932.

The data management module 944, based on the enterprise identifier, forwards the signals to the appropriate compliance database 936, or storage location(s), for storage and analysis. As will be appreciated, the module 944 maps the monitored entity identifier against a lookup table indexing monitored entity identifiers against database address and/or storage address range. The received information is then forwarded to an interface for the corresponding database for storage. The table is further used to retrieve compliance data for an identified, monitored entity.

In another embodiment, the data management module 944 and/or compliance filter 920 use location information to identify appropriate compliance monitor(s) 916a, b-p to which to report, to configure collection parameters, and/or to configure compliance reports for transmission to the identified compliance monitor(s) 916a, b-p. The location information can be in many different forms. For example, each monitored facility of a common enterprise or each monitored enterprise is assigned geographical information indicating the physical location of the monitored entity. In another example, each monitored facility of a common enterprise or each monitored enterprise is assigned geopolitical information indicating the regulatory jurisdiction or political location of the monitored entity. By way of illustration, the political location of the facility would identify each compliance monitor 916a, b-p to which activities at the facility must be reported. In yet another example, each washing station is assigned geographic and/or geopolitical information. In yet another example, each washing station has an embedded location module, such as a GPS or other satellite enabled locating device, which provides location coordinates. In this example, as the washing station is moved from one facility to another the location information is changed dynamically.

Using the location information, whether associated with the facility as a whole or separately with each washing station in the facility, the data management module 944 determines the corresponding monitoring and reporting requirements for the pertinent compliance monitor(s) 916a, b-p. This is typically done using a lookup table, such as that shown in FIG. 12.

Referring to FIG. 12, the geographic location information 1200 is mapped against compliance monitor 1202, compliance data required 1204, required reporting frequency 1208, and reporting requirements 1212. The geographic location information 1200 refers to the expression of geographical and/or geopolitical location used to signify the location of the monitored entity. As noted, the geographic location information 1200 can be satellite-enabled location coordinates, compliance monitor identifiers, city identifiers, county identifiers, state identifiers, country identifiers, and the like. The compliance monitor designation 1202 identifies the compliance monitor 916a, b-p to which compliance reports are to be provided. The values in column 1202 can be values associated with the compliance monitor 916a, b-p (which may be an electronic address). Compliance data required 1204 refers to the information to be collected to comply with requirements of the identified compliance monitor. Compliance data required 1204 includes, for example, a number of required washes/station, percent compliance (determined on a suitable basis), number of required washes/employee, and the like.

The required reporting frequency 1208 refers to how frequently compliance data/reports are to be forwarded to the identified compliance monitor. The frequency, for example, can be daily, weekly, monthly, yearly, and the like. Finally, report requirements 1212 refer to requirements for the compliance information provided to the identified compliance monitor. Report requirements 1212, for example, can refer to how the compliance data is to be transmitted to the monitor (e.g., by email, by mail, by upload/download operation over the data network 924, and the like), the formatting and organizational requirements for the report, the entities associated with the monitor to whom the information is to be provided and each entity's address information, and the like. Other information in column 12 includes whether the information is to be encrypted and, if so, what key(s) are to be employed, the human or computer language in which the report is to be expressed (e.g., German, English, HTML, XML, and the like), and the like.

Figure 13:
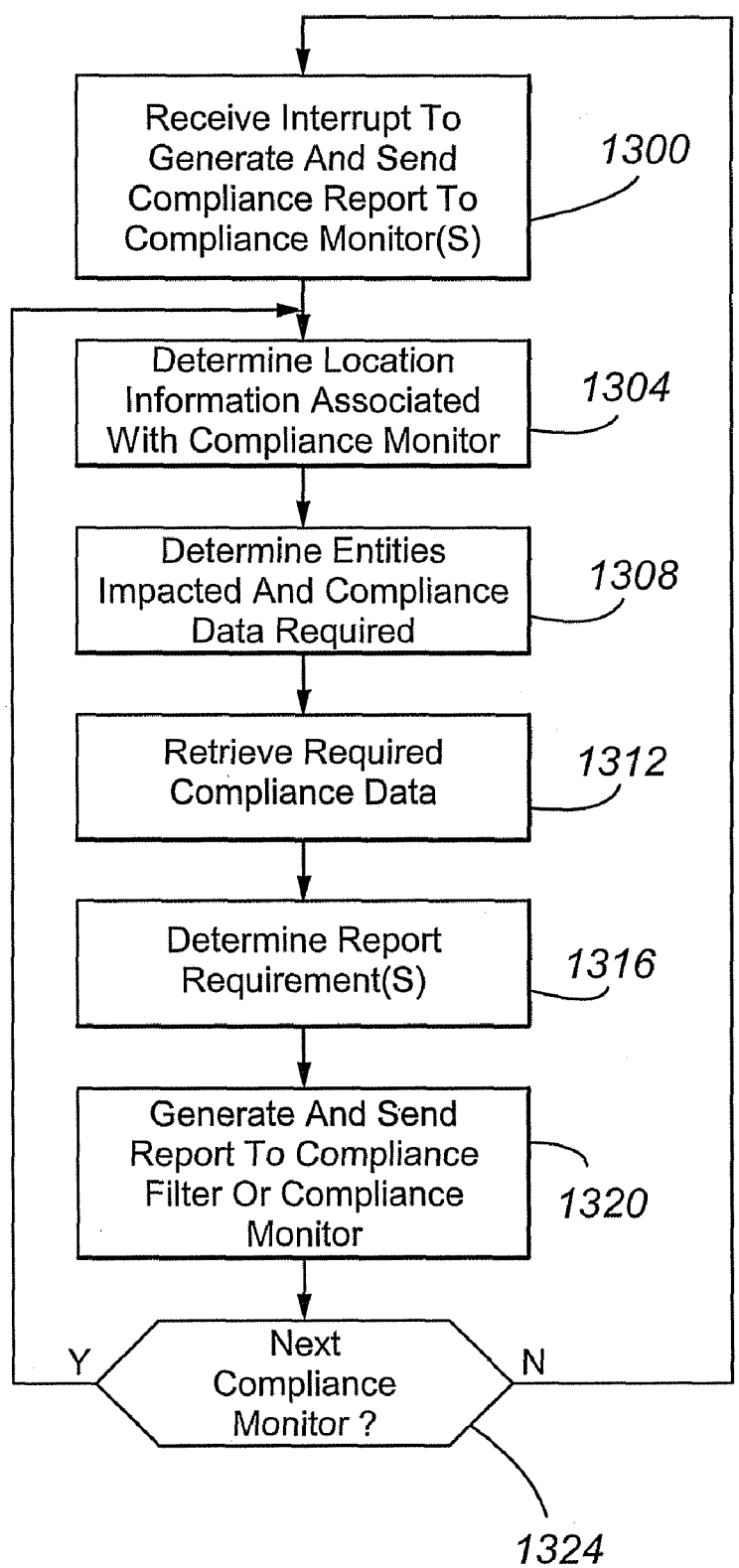
FIG. 13 is a flow chart according to an embodiment of the present invention; The drawings are not necessarily to scale.

The operation of this embodiment will now be discussed with reference to FIG. 13.

In step 1300, a scheduling module (not shown) generates an interrupt identifying one or more compliance monitors 916a, b-p requiring compliance report(s) to be provided. The interrupt is received by the data management module 944.

In step 1304, the module 944 determines the location information associated with a selected one of the compliance monitors referenced in the interrupt. This can be done by mapping an identifier of the selected compliance monitor against a listing of location information regulated or serviced by the selected compliance monitor 916a, b-p.

In step 1308, the module 944 determines, based on the geographic location information 1200, each of the monitored entities 904a,b-w monitored by the selected compliance monitor and, based on the geographic location information 1200 a monitored entity identifier for each of the identified entities, the compliance data required 1204.

In step 1312, the module 944 retrieves the required compliance data. This is typically done iteratively on an enterprise-by-enterprise basis to avoid intermixing compliance data for different enterprises. Compliance data may be collected by querying the appropriate one of the first, second, . . . nth databases 936a-n and/or obtaining compliance information from each of the first, . . . xth washing stations 100a-x at the subject facility for each identified enterprise.

In step 1316, the module 944 determines the reporting requirements 1212 for the selected compliance monitor.

In step 1320, the module 944, using the reporting requirements and compliance data obtained, generates and sends the report to the compliance filter 920 and/or directly to the compliance monitor 916a, b-p. When the report is sent to the compliance filter 920, the filter 920 can remove unnecessary information collected by the washing stations and forward the filtered report to the compliance monitor 916a, b-p.

In decision diamond 1324, the module 944 determines whether the interrupt identified a next compliance monitor. If not, control returns to step 1300. If so, the next compliance monitor is selected, and the module returns to step 1304.

The following U.S. patents are incorporated herein by reference in their entireties U.S. Pat. Nos. 823,447; 5,265,628; 4,817,651; and 4,925,495.

Though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Moreover, various other aspects of the invention disclosed herein are set out in the following numbered clauses:

1. An automated washing compliance verification system provided in association with a plurality of enterprise networks, the system comprising:

a plurality of washing stations each operable to wash an object, the plurality of washing stations being associated with the plurality of enterprise networks; and a compliance data hub including a memory, the memory comprising:

(a) a data management module; and (b) a plurality of electronic storage locations, each storage location being associated with a corresponding enterprise network and storing compliance data collected by at least one washing station in the corresponding enterprise network;

wherein the data management module is operable to produce a data management report including compliance data collected in at least one enterprise network of the plurality of enterprise networks.

2. The automated washing compliance verification system of clause 1, wherein each enterprise network has a corresponding unique enterprise identifier and wherein each storage location is associated with a different enterprise identifier.

3. The automated washing compliance verification system of clause 2, wherein each washing station has a corresponding station identifier, with each station identifier being unique in the enterprise network containing the washing station.

4. The automated washing compliance verification system of clause 1, wherein the compliance data comprises a plurality of different object identifiers and different protocol identifiers, each protocol identifier being associated with a different cleaning protocol.

5. The automated washing compliance verification system of clause 4, wherein each object identifier has a corresponding protocol identifier and wherein at least one protocol identifier indicates that no cleaning be performed for the corresponding object identifier.

6. The automated washing compliance verification system of clause 1, wherein the data management module is operable to provide the data management module report to a web user, the web user having supplied a valid password.

7. The automated washing compliance verification system of clause 1, wherein the data management module is operable to provide the data management module report to a compliance monitor.

8. The automated washing compliance verification system of clause 7, wherein the compliance monitor includes at least one of:

a city government entity;

a state government entity;

a federal government entity; and a private compliance monitoring entity.

9. The automated washing compliance verification system of clause 7, further comprising:

a compliance filter operable to filter compliance data prior to the data being provided to the compliance monitor.

10. The automated washing compliance verification system of clause 9, wherein the compliance filter modifies at least one data item from the compliance data.

11. The automated washing compliance verification system of clause 1, wherein the data management module reports one or more entries, the entries including at least one of:
an enterprise identifier;
a station identifier;
a user identifier;
a date;
a time;
a facility identifier;
a compliance monitor identifier; and
a compliance indicator.

12. The automated washing compliance verification system of clause 1, wherein the plurality of business enterprises include a first and a second business enterprise, the first and second business enterprise being separately owned.

13. The automated washing compliance verification system of clause 12, wherein the first enterprise includes a plurality of discrete facilities.

14. The automated washing compliance verification system of clause 1, wherein each enterprise network includes a custom report module in communication with the data management module associated with the compliance data hub, each custom report module being enabled by a token imported from the compliance data hub, the token including at least one of:
a company name;
primary contact information;
secondary contact information;
number of licensed users; and
type of service supported.

15. The automated washing compliance verification system of clause 1, wherein the data management module is operable to provide an analysis of the compliance data, and based on the analysis, provide at least one alarm to at least one enterprise network.

16. The automated washing compliance verification system of clause 1, wherein the compliance data associated with a particular enterprise network includes data collected by a security system associated with the particular enterprise network.

17. The automated washing compliance verification system of clause 1, wherein the at least one washing station includes:
(a) an identification apparatus operatively associated with the washing station, the identification apparatus operable to at least automatically identify at least one of:
(1) the user, and
(2) an object;
(b) a washing station operations monitor operatively associated with the cleaning station and the identification apparatus; and
(c) a memory associated with the washing station operations monitor, the memory comprising at least one of:
(1) a compliance module operable to record data associated with the user;
(2) an information module operable to provide the user with at least one segment of information about at least one of entertainment, a cleaning history statistic, and training;
(3) a consumables-authentication module operable to verify that the washing station is operating with a particular substance; and
(4) a solutions selection module operable to direct the washing station to perform at least one of the following:
(A) based on a user identifier, administer at least one of:
(i) a predetermined mixture; and
(ii) a substance;
and
(B) operate a function for a predetermined period of time based on a history of washing compliance for the user.

18. In a hygiene compliance verification system, a computer readable medium comprising a set of data structures, the set of data structures comprising:
(a) a first set of information identifying a hygiene compliance monitor;
(b) compliance data required to be reported to the compliance monitor; and
(c) reporting requirements associated with the compliance monitor;
wherein the data structures are used to produce a data management report including the compliance data.

19. The medium of clause 18, wherein the set of data structures further comprises:
a reporting frequency required by the compliance monitor.

20. The medium of clause 18, wherein the set of data structures further comprises:
location information, the location information identifying at least one of a geographical and geopolitical location monitored by the compliance monitor.

21. A compliance monitoring system for use with at least one hygiene station, the system comprising;
(a) a verification module; and
(b) an electronic storage location for storing compliance data collected by the at least one hygiene station, wherein the compliance data comprises a plurality of different object identifiers and different protocol identifiers, each protocol identifier being associated with a different cleaning protocol, wherein each object identifier has a corresponding protocol identifier and wherein at least one protocol identifier indicates that no cleaning be performed for the corresponding object identifier.

22. The system of clause 21, further comprising:
a plurality of enterprise networks, each enterprise network including at least one corresponding hygiene station; and
a plurality of electronic storage locations, each storage location being associated with a corresponding enterprise network and storing compliance data collected by the at least one corresponding hygiene station in the corresponding enterprise network.

23. The system of clause 22, wherein each enterprise network has a corresponding unique identifier and wherein each storage location is associated with a different enterprise identifier.

24. The system of clause 23, wherein each hygiene station has a corresponding station identifier, with each station identifier being unique in the enterprise network containing the hygiene station.

25. The system of clause 21, wherein the hygiene station comprises a sink and a faucet, and wherein the compliance monitoring system further comprises at least one sensor at or proximate to at least one of the sink and the faucet.

26. The system of clause 21, wherein the hygiene station comprises an automated cleaning station, and wherein the compliance monitoring system further comprises at least one sensor at or proximate to the automated cleaning station.

27. The system of clause 21, further comprising a compliance filter, wherein the compliance filter receives the compliance data and filters the compliance data before it is provided to one or more compliance monitors.

28. A compliance monitoring system, comprising:
   means for receiving compliance data associated with a plurality of enterprise networks;
   means for storing the compliance data in a plurality of electronic storage locations, wherein each storage location corresponds to one enterprise network of the plurality of enterprise networks; and
   means for providing at least one compliance data report, the compliance data report including compliance data received from a particular enterprise network of the plurality of enterprise networks.

29. The compliance monitoring system of clause 28, further comprising:
   means for providing the compliance data report to a web user, the web user having supplied a valid password.

30. The compliance monitor of clause 28, further comprising:
   means for providing the compliance data report to a compliance monitor.

31. A method of performing hygiene compliance verification, comprising:
   receiving hygiene compliance data associated with a plurality of enterprise networks, each network being associated with a different enterprise comprising one or more automated sensors;
   storing the hygiene compliance data; and
   providing at least one hygiene compliance data report, the hygiene compliance data report including hygiene compliance data received from a particular enterprise network of the plurality of enterprise networks.

32. The method of clause 31, further comprising:
   providing the hygiene compliance data report to a web user, the web user having supplied a valid password.

33. The method of clause 31, further comprising:
   providing the hygiene compliance data report to a compliance monitor.

34. The method of clause 33, wherein the compliance monitor includes at least one of:
   a city government entity;
   a state government entity;
   a federal government entity; and
   a private compliance monitoring entity.

35. The method of clause 33, further comprising:
   prior to providing the hygiene compliance data report to the compliance monitor, filtering the hygiene compliance data, wherein filtering includes removing at least one data item from the hygiene compliance data.

36. The method of clause 31, further comprising:
   analyzing the hygiene compliance data; and
   based on the analysis, providing at least one alarm to at least one enterprise network.

37. The method of clause 31, wherein the hygiene compliance data associated with a particular enterprise network includes data collected by a security system associated with the particular enterprise network.

38. The method of clause 31, wherein an automated sensor in each enterprise network compiles the hygiene compliance data by:
   automatically identifying a user of at least a first cleaning station, the cleaning station including an apparatus for automatically washing at least a portion of the user; and
   recording by a computer at least an identity of the user of the first cleaning station, the first cleaning station automatically washing at least the portion of the user.

39. The method of clause 31, wherein the hygiene compliance data is stored in a plurality of electronic storage locations, each storage location corresponding to one of the plurality of enterprise networks.

40. A method for reporting hygiene compliance, comprising:
   (a) determining automatically a geographic location information associated with a compliance monitor;
   (b) determining automatically a monitored entity identifier associated with the geographic location information, the monitored entity identifier being associated with at least one of an enterprise and a facility;
   (c) determining automatically hygiene compliance data required by the compliance monitor;
   (d) based on the hygiene compliance data required, providing hygiene compliance data associated with the monitored entity identifier;
   (e) determining automatically report requirements associated with the compliance monitor; and
   (f) forwarding the provided hygiene compliance data to the compliance monitor.

41. A computer readable medium operable to perform the steps of clause 40.

42. A method for performing hygiene compliance verification, comprising:
   (a) receiving an object identifier;
   (b) determining a cleaning protocol from a plurality of different protocols to be used on an object associated with the object identifier; and
   (c) implementing the cleaning protocol in connection with the object.

43. The method of clause 42, wherein the object identifier indicates that no cleaning is required.

44. The method of clause 42, wherein implementing the cleaning protocol includes:
   (i) cleaning the identified object in accordance with the cleaning protocol; and
   (ii) generating a compliant and/or noncompliant signal indicating compliance and/or noncompliance with at least part of the cleaning protocol.

45. The method of clause 42, wherein the object identifier is associated with an object type identifier.

46. The method of clause 45, wherein the object type identifier is indicative of a type of employee.

47. An electronic hygiene compliance verification data signal, comprising:
   (a) source and destination addresses;
   (b) hygiene compliance information; and
   (c) an enterprise identifier; and
   (d) a compliance monitor identifier.

48. The data signal of clause 47, wherein the hygiene compliance information comprises a station identifier.

49. The data signal of clause 47, wherein the hygiene compliance information comprises a user identifier.

50. The data signal of clause 47, wherein the hygiene compliance information comprises one or more of a date and a time.

51. The data signal of clause 47, wherein the hygiene compliance information comprises a facility identifier.

52. The data signal of clause 47, wherein the hygiene compliance information comprises a compliance confirmation.

53. The data signal of clause 47, wherein the hygiene compliance information comprises hygiene compliance data received from a particular enterprise network of a plurality of enterprise networks, the particular enterprise network associated with the enterprise identifier 54. The data signal of clause 47, further comprising at least a second enterprise identifier.

55. The data signal of clause 54, wherein the hygiene compliance information comprises hygiene compliance data received from a particular enterprise network of a plurality of enterprise networks, the particular enterprise network associated with the enterprise identifier, the plurality of enterprise networks including at least a second enterprise network, wherein the second enterprise identifier is associated with the second enterprise network.

56. The data signal of clause 47, wherein the compliance monitor identifier is associated with at least one of:
a city government entity;
a state government entity;
a federal government entity; and
a private compliance monitoring entity.

57. The data signal of clause 47, wherein the hygiene compliance information includes information associated with a hygiene station comprising a sink and a faucet, wherein the hygiene station further comprises at least one sensor at or proximate to at least one of the sink and the faucet.

58. The data signal of clause 47, wherein the hygiene compliance information includes information associated with a hygiene station comprising an automated cleaning station, wherein the hygiene station further comprises at least one sensor at or proximate to the automated cleaning station.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

What is claimed is:

1. An automated washing compliance verification system provided in association with a plurality of enterprise networks, each enterprise network being associated with a different company, the system comprising:
a plurality of washing stations each operable to wash an object, the plurality of washing stations being associated with the plurality of enterprise networks; and
a compliance data hub including a memory, the memory comprising:
(a) a data management module operable to provide a data management module report; and
(b) a plurality of electronic storage locations, each storage location being associated with a corresponding enterprise network and storing compliance data collected by at least one washing station in the corresponding enterprise network;
wherein the data management report includes compliance data collected in at least one enterprise network of the plurality of enterprise networks.

2. The automated washing compliance verification system of claim 1, wherein each enterprise network has a corresponding unique enterprise identifier and wherein each storage location is associated with a different enterprise identifier.

3. The automated washing compliance verification system of claim 2, wherein each washing station has a corresponding station identifier, with each station identifier being unique in the enterprise network containing the washing station.

4. The automated washing compliance verification system of claim 1, wherein the compliance data comprises a plurality of different object identifiers and different protocol identifiers, each protocol identifier being associated with a different cleaning protocol.

5. The automated washing compliance verification system of claim 1, wherein the different companies are different health care providers and wherein the data management module is operable to provide the data management module report to a web user, the web user having supplied a valid password.

6. The automated washing compliance verification system of claim 1, wherein the data management module is operable to provide the data management module report to a compliance monitor, the compliance monitor monitoring compliance of the corresponding company with a set of hygiene requirements.

7. The automated washing compliance verification system of claim 1, wherein the data management module reports one or more entries, the entries including at least most of the following:
an enterprise identifier;
a station identifier;
a user identifier;
a date;
a time;
a facility identifier;
a compliance monitor identifier; and
a compliance indicator.

8. The automated washing compliance verification system of claim 1, wherein the plurality of business enterprises include a first and a second business enterprise, the first and second business enterprise being separately owned.

9. The automated washing compliance verification system of claim 1, wherein each enterprise network includes a custom report module in communication with the data management module associated with the compliance data hub, each custom report module being enabled by a token imported from the compliance data hub, the token including at least one of:
a company name;
primary contact information;
secondary contact information;
number of licensed users; and
type of service supported.

10. The automated washing compliance verification system of claim 1, wherein the data management module is operable to provide an analysis of the compliance data, and based on the analysis, provide at least one alarm to at least one enterprise network.

11. The automated washing compliance verification system of claim 1, wherein the compliance data associated with a particular enterprise network includes data collected by a security system associated with the particular enterprise network.

12. The automated washing compliance verification system of claim 1, wherein the at least one washing station includes:
   (a) an identification apparatus operatively associated with the washing station, the identification apparatus operable to at least automatically identify at least one of:
      (1) a user, and
      (2) an object;
   (b) a washing station operations monitor operatively associated with the cleaning station and the identification apparatus; and
   (c) a memory associated with the washing station operations monitor, the memory comprising at least one of:
      (1) a compliance module operable to record data associated with the user;
      (2) an information module operable to provide the user with at least one segment of information about at least one of entertainment, a cleaning history statistic, and training;
      (3) a consumables-authentication module operable to verify that the washing station is operating with a particular substance; and
      (4) a solutions selection module operable to direct the washing station to perform at least one of the following:
         (A) based on a user identifier, administer at least one of:
            (i) a predetermined mixture; and
            (ii) a substance; and
         (B) operate a function for a predetermined period of time based on a history of washing compliance for the user.

13. In a hygiene compliance verification system, a computer readable medium comprising a set of data structures, the set of data structures comprising:
   (a) a first set of information identifying a hygiene compliance monitor from among a plurality of possible hygiene compliance monitors;
   (b) compliance data required to be reported to the corresponding compliance monitor of the plurality of compliance monitors; and
   (c) reporting requirements associated with each of the compliance monitors, each of the compliance monitors having different reporting requirements;
wherein the data structures are used to produce, for the corresponding compliance monitor, a data management report including the compliance data.

14. The medium of claim 13, wherein the set of data structures further comprises:
   a reporting frequency required by the compliance monitor.

15. The medium of claim 13, wherein the set of data structures further comprises:
   location information, the location information identifying at least one of a geographical and geopolitical location monitored by the compliance monitor.

16. A method for reporting hygiene compliance, comprising:
   (a) determining automatically geographic location information associated with a selected compliance monitor, each of a plurality of compliance monitors corresponding to different geographic location information;
   (b) determining automatically a monitored entity identifier associated with the geographic location information, the monitored entity identifier being associated with at least one of an enterprise and a facility;
   (c) determining automatically hygiene compliance data required by the selected compliance monitor;
   (d) based on the hygiene compliance data required, providing hygiene compliance data associated with the monitored entity identifier;
   (e) determining automatically report requirements associated with the selected compliance monitor, each of the compliance monitors being associated with different report requirements; and
   (f) forwarding the provided hygiene compliance data to the selected compliance monitor.

17. The method of claim 16, wherein each of the compliance monitors is a governmental entity.

18. A washing compliance verification system having a processor for processing an electronic hygiene compliance verification data signal, the electronic hygiene compliance verification data signal comprising:
   (a) source and destination addresses;
   (b) hygiene compliance information; and
   (c) an enterprise identifier associated with a business, a plurality of unique enterprise identifiers being associated with a plurality of different businesses; and
   (d) a compliance monitor identifier, a plurality of different compliance monitor identifiers being associated with a plurality of different compliance monitors.

19. The system of claim 18, wherein the hygiene compliance information comprises a station identifier.

20. The system of claim 18, wherein the hygiene compliance information comprises a user identifier.

21. The system of claim 18, wherein the hygiene compliance information comprises one or more of a date and a time.

22. A system, comprising:
   (a) at least one administration computer associated with a plurality of wash stations, each wash station having a unique station identifier;
   (b) a compliance data hub operable to collect cleaning information from the administration computer;
   (c) a data management module operable to select a compliance monitor from among a plurality of possible compliance monitors, determine report requirements for the selected compliance monitor, and convert the collected cleaning information into a compliance report in accordance with the report requirements; and
   (d) a compliance monitor operable to receive the compliance report, the compliance monitor being a governmental entity.

23. The system of claim 22, further comprising a plurality of monitored entities, each monitored entity comprising the wash stations and having a unique monitored entity identifier and each of the monitored entities being associated with a business and wherein each of the monitored entities are discrete facilities associated with the business.

24. The system of claim 22, further comprising a plurality of compliance modules associated with the plurality of wash stations, each of the compliance modules receiving a user identifier from a user, determining a suitable cleaning protocol from a plurality of possible cleaning protocols, and records cleaning information respecting a cleaning interaction with the user.

25. The system of claim 23, wherein the data management module determines the report requirements using geographic location information with respect to a selected monitored entity associated with the cleaning information.

* * * * *